United States Patent
Li et al.

(10) Patent No.: US 11,512,056 B2
(45) Date of Patent: Nov. 29, 2022

(54) GUANIDYL-CONTAINING P2Y12 RECEPTOR ANTAGONIST AND PREPARATION METHOD AND APPLICATION THEREOF

(71) Applicant: Anhui New Star Pharmaceutical Development Co., Ltd, Hefei (CN)

(72) Inventors: Xiaoxiang Li, Hefei (CN); Ziao Xu, Hefei (CN); Degang Li, Hefei (CN); Yumei Xu, Hefei (CN); Yonghai Zhao, Hefei (CN); Genling Jiang, Hefei (CN)

(73) Assignee: Anhui New Star Pharmaceutical Development Co., Ltd, Hefei (CN)

( * ) Notice: Subject to any disclaimer, the term of this patent is extended or adjusted under 35 U.S.C. 154(b) by 62 days.

(21) Appl. No.: 17/105,445

(22) Filed: Nov. 25, 2020

(65) Prior Publication Data

US 2021/0078954 A1 Mar. 18, 2021

Related U.S. Application Data

(63) Continuation of application No. PCT/CN2019/074313, filed on Feb. 1, 2019.

(30) Foreign Application Priority Data

Feb. 5, 2018 (CN) .......................... 201810115116.8

(51) Int. Cl.
*C07D 237/04* (2006.01)
*A61P 7/02* (2006.01)

(52) U.S. Cl.
CPC .............. *C07D 237/04* (2013.01); *A61P 7/02* (2018.01)

(58) Field of Classification Search
CPC .................................................... C07D 237/04
See application file for complete search history.

(56) References Cited

U.S. PATENT DOCUMENTS

| | | | |
|---|---|---|---|
| 4,521,415 A | 6/1985 | Katakami et al. | |
| 4,921,856 A * | 5/1990 | Schickaneder | ...... C07D 237/04 544/239 |
| 4,946,842 A | 8/1990 | Coates et al. | |
| 4,968,683 A * | 11/1990 | Morsdorf | ............. C07D 401/14 514/218 |

FOREIGN PATENT DOCUMENTS

AU 2006260666 A1 12/2006

OTHER PUBLICATIONS

Banker et al. (1994).*
Wolff et al (994).*
Vippagunta et al. (2001).*
First Office Action issued in corresponding Chinese Application No. 201810115116.8; dated Apr. 8, 2022; 17 pgs.

* cited by examiner

*Primary Examiner* — Paul V Ward
(74) *Attorney, Agent, or Firm* — Nitin Kaushik

(57) ABSTRACT

A P2Y12 receptor antagonist containing a guanidyl, and a preparation method and the use thereof. In particular, the present disclosure provides a pyridazinone-guanidine compound that is a compound of structural formula (I), or a stereoisomer of the above-mentioned compound, a pro-drug thereof, a pharmaceutically acceptable salt thereof or a pharmaceutically acceptable solvate thereof. Such a compound has multiple pharmacological activities, especially has an inhibitory effect on platelet aggregation, and can be used for preparing an anti-platelet aggregation pharmaceutical composition.

2 Claims, 3 Drawing Sheets

GUANIDYL-CONTAINING P2Y12 RECEPTOR ANTAGONIST AND PREPARATION METHOD AND APPLICATION THEREOF

CROSS-REFERENCE TO RELATED APPLICATIONS

The present application is a Continuation of International Application Number PCT/CN2019/074313, filed Feb. 1, 2019, and claims priority to Chinese patent application No. 201810115116.8, filed on Feb. 5, 2018, the entire contents of which are both incorporated herein by their reference.

TECHNICAL FIELD

The present disclosure provides a pyridazinone-guanidine compound or a pharmaceutically acceptable salt, solvate, ester, acid, metabolite or prodrug thereof, and also provides a pharmaceutical composition containing the compound, and use in the role for treating related diseases.

BACKGROUND

Thrombotic diseases are a serious threat to human life and health. Its incidence is the highest among various diseases, and it has been increasing in recent years. It is one of the focuses and hotspots of contemporary medical research. Thrombosis refers to the pathological process in which formed components of blood form emboli in blood vessels (mostly small blood vessels) under certain conditions, causing partial or complete blockage of blood vessels and impaired blood supply to corresponding parts. There are many factors that cause thrombotic diseases, and the increase of platelet activity is an important factor leading to thrombosis.

Platelets are produced by megakaryocytes, which play an important role in the initial hemostasis and thrombosis. The activation, aggregation, and release of platelets are closely related to the pathophysiological mechanism of ischemic cerebrovascular disease. The prevention and treatment of stroke and acute coronary syndrome (ACS) are based on multiple mechanisms and acting on different targets. Its value has been confirmed by a large number of clinical trials. At present, antiplatelet therapy has become an important strategy for the prevention and treatment of thrombosis in the arterial system. Antiplatelet therapy is launched for different links in the process of platelet activation. With the in-depth understanding of the mechanism of platelet activation, more understanding of signal transduction pathways is provided. Antiplatelet therapy provides new ideas.

At present, adenosine diphosphate (ADP) receptor inhibitors are an important class of anti-platelet aggregation drugs, and P2Y12 receptor antagonists are the most widely used ADP receptor inhibitors. Antiplatelet aggregation plays an important role in the prevention and treatment of coronary heart disease. As an important part of antiplatelet aggregation drugs, P2Y12 receptor antagonists have a wide range of clinical applications. In the choice of anti-platelet aggregation drugs, not only should the clinical efficacy of the drugs be considered, but also the adverse effects and safety of the drugs should be weighed, and the individual differences of patients should be considered, so as to formulate the most suitable treatment plan to maximize the benefit of patients.

Since the discovery of pyridazinone compounds in the 1960s, it has been found to have anti-platelet aggregation activity, as well as anti-cancer, anti-hypertensive, anti-convulsant, cardiotonic, antibacterial, anti-inflammatory, analgesic, herbicide and insecticide. active. Through our research, we discovered a new type of pyridazinone compound that can act on the P2Y12 receptor and has a very good anti-platelet aggregation effect.

SUMMARY

A purpose of the present disclosure is to provide a new type of pyridazinone compound with good anti-platelet aggregation activity and processes of preparing method and application.

In one aspect, the present disclosure provides a pyridazinone-guanidine compound, or a stereoisomer of the above compound, a pro-drug, a pharmaceutically acceptable salt or a pharmaceutically acceptable solvate thereof, wherein structure of the compound is shown in general Formula (I):

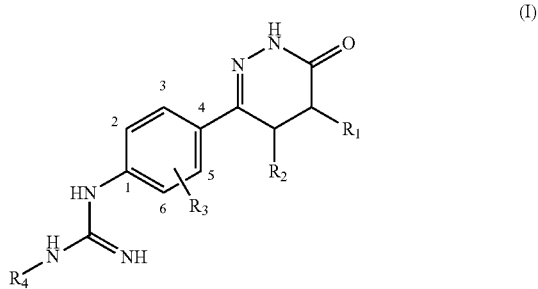

wherein:
the positions on the benzene ring are numbered 1-6,
R1 is selected from: hydrogen, halogen, nitro, cyano; C1-C6 alkyl optionally substituted by halogen, nitro, cyano; C1-C6 oxygen-containing alkyl; C3-C7 cycloalkyl optionally substituted by halogen, nitro, cyano; —O—C1-C6 alkyl optionally substituted by halogen, nitro, amino, cyano; —O—C3-C7 cycloalkyl optionally substituted by halogen, nitro, amino, cyano; C6-C10 aryl optionally substituted by halogen, nitro, amino, cyano; —O—C6-C10 aryl optionally substituted by halogen, nitro, amino, cyano; C2-C6 alkenyl;
R2 is selected from: hydrogen, halogen, nitro, cyano; C1-C6 alkyl optionally substituted by halogen, nitro, cyano; C1-C6 oxygen-containing alkyl; C3-C7 cycloalkyl optionally substituted by halogen, nitro, cyano; —O—C1-C6 alkyl optionally substituted by halogen, nitro, amino, cyano; —O—C3-C7 cycloalkyl optionally substituted by halogen, nitro, amino, cyano; C6-C10 aryl optionally substituted by halogen, nitro, amino, cyano; —O—C6-C10 aryl optionally substituted by halogen, nitro, amino, cyano; C2-C6 alkenyl;
R3 is selected from: hydrogen, halogen, nitro, cyano, amino, hydroxyl; substituted or unsubstituted C1-C6 alkyl, substituted or unsubstituted C3-C7 cycloalkyl, C3-C7 cycloalkyl, C1-C6 Alkyl, heterocyclylC1-C6 alkyl, substituted or unsubstituted C6-C10 aryl, C9-C12 bicyclic aryl, heteroC6-C12 bicyclic aryl, heteroC6-C12 bicyclic arylC1-C3 alkyl, C6-C10 aryl C1-C3 alkyl, substituted or unsubstituted C6-C10 aryl C1-C6 alkyl, substituted or unsubstituted heteroaryl, substituted or unsubstituted heteroarylC1-C6 alkyl, carbonylC1-C6 alkyl, thiocarbonylC1-C6 alkyl, sulfonylC1-C3 alkyl, sulfinylC1-C6 alkyl, iminoC1-C6 alkyl, —O—C1-C6 alkyl; and
R4 is selected from: hydrogen; C1-C6 alkyl optionally substituted by halogen, nitro, cyano; C1-C6 oxygen-containing alkyl; C3-C7 cycloalkyl optionally substituted by halogen, nitro, cyano; —O—C1-C6 alkyl optionally substituted by halogen, nitro, amino, cyano; —O—C3-C7 cycloalkyl optionally substituted by halogen, nitro, amino, cyano; C6-C10 aryl optionally substituted by halogen, nitro, amino, cyano; —O—C6-C10 aryl optionally substituted by halogen, nitro, amino, cyano; C2-C6 alkenyl; C3-C6 acyl; C1-C6 alkylsulfonyl.

In another aspect, the present disclosure provides a pharmaceutical composition comprising the above-mentioned compound and optionally pharmaceutical acceptable excipients.

In another aspect, the present disclosure provides a process for preparing the above-mentioned compound and a use of the above-mentioned compound in preparation of a medicament for anti-platelet aggregation, a use for preparing a medicament for the treatment of cardiovascular and cerebrovascular, especially thromboembolic diseases, and a use of preparing inhibitors for platelet activation, platelet aggregation and platelet degranulation, and a use as an accelerator for platelet depolymerization.

DETAILED DESCRIPTION OF THE EMBODIMENTS

Figure 1:
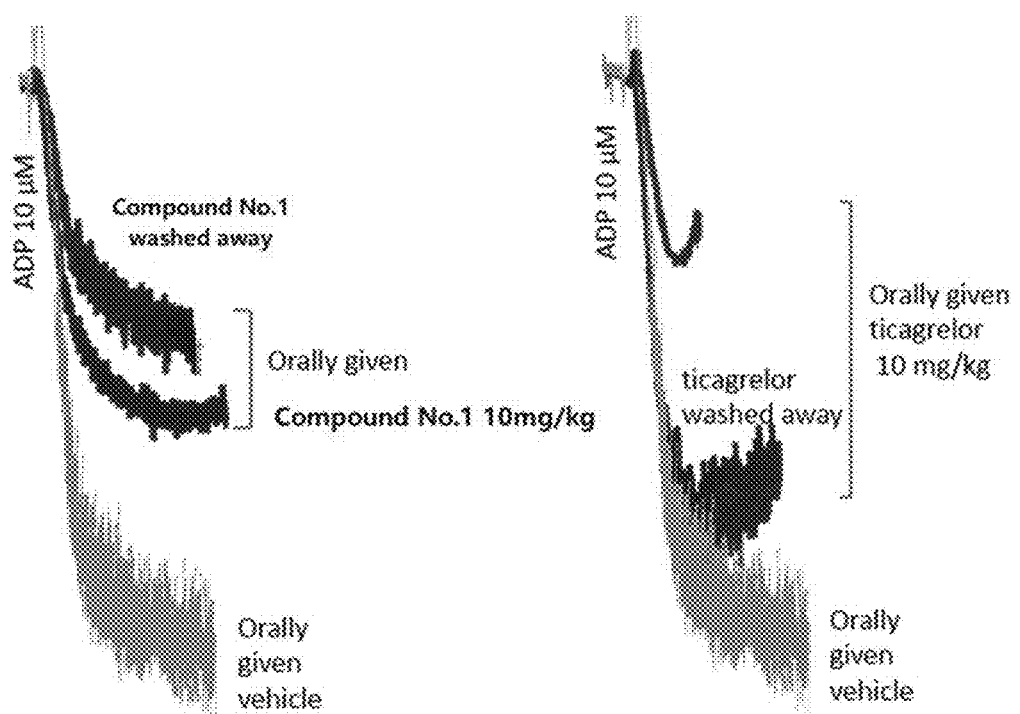
FIG. 1 is a comparison of the effects of the reversible P2Y12 inhibitor ticagrelor and the irreversible P2Y12 inhibitor No. 1 compound on ADP-induced platelet aggregation.
Figure 2:
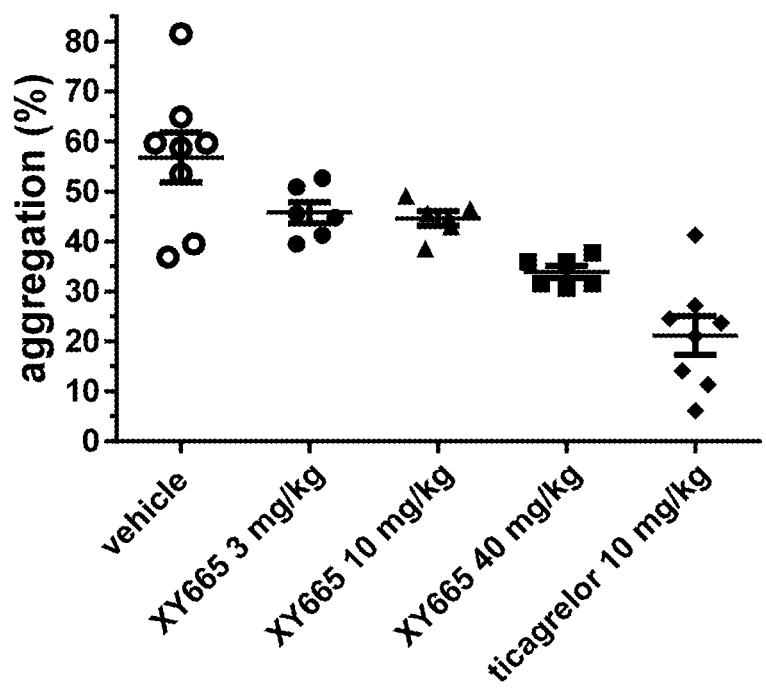
FIG. 2 is the description of No. 1 compound dose lazily inhibits ADP-induced platelet aggregation.
Figure 3:
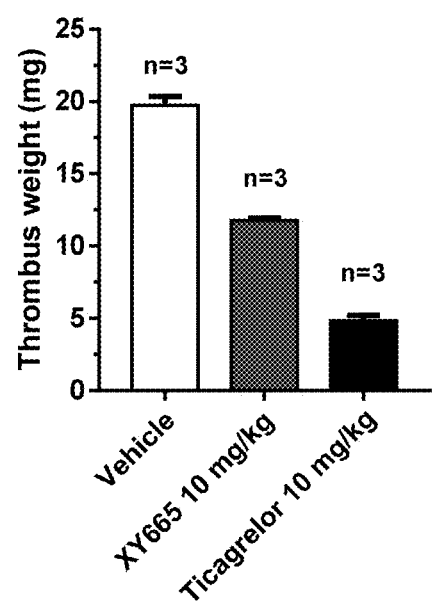
FIG. 3 is the description of the effect of compound No. 1 on the atrioventricular bypass artery thrombosis model

The present disclosure provides a pyridazinone-guanidine compound, or a stereoisomer of the mentioned compound, a pro-drug, a pharmaceutically acceptable salt or a pharmaceutically acceptable solvate thereof, the structure of the compound may be presented by the following general Formula (I):

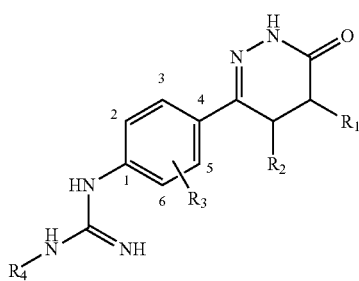

wherein: the positions on the benzene ring are numbered 1-6,

R1 is selected from: hydrogen, halogen, nitro, cyano; C1-C6 alkyl optionally substituted by halogen, nitro, cyano; C1-C6 oxygen-containing alkyl; C3-C7 cycloalkyl optionally substituted by halogen, nitro, cyano; —O—C1-C6 alkyl optionally substituted by halogen, nitro, amino, cyano; —O—C3-C7 cycloalkyl optionally substituted by halogen, nitro, amino, cyano; C6-C10 aryl optionally substituted by halogen, nitro, amino, cyano; —O—C6-C10 aryl optionally substituted by halogen, nitro, amino, cyano; C2-C6 alkenyl;

R2 is selected from: hydrogen, halogen, nitro, cyano; C1-C6 alkyl optionally substituted by halogen, nitro, cyano; C1-C6 oxygen-containing alkyl; C3-C7 cycloalkyl optionally substituted by halogen, nitro, cyano; —O—C1-C6 alkyl optionally substituted by halogen, nitro, amino, cyano; —O—C3-C7 cycloalkyl optionally substituted by halogen, nitro, amino, cyano; C6-C10 aryl optionally substituted by halogen, nitro, amino, cyano; —O—C6-C10 aryl optionally substituted by halogen, nitro, amino, cyano; C2-C6 alkenyl;

R3 is selected from: hydrogen, halogen, nitro, cyano, amino, hydroxyl; substituted or unsubstituted C1-C6 alkyl, substituted or unsubstituted C3-C7 cycloalkyl, C3-C7 cycloalkyl, C1-C6 Alkyl, heterocyclylC1-C6 alkyl, substituted or unsubstituted C6-C10 aryl, C9-C12 bicyclic aryl, heteroC6-C12 bicyclic aryl, heteroC6-C12 bicyclic arylC1-C3 alkyl, C6-C10 aryl C1-C3 alkyl, substituted or unsubstituted C6-C10 aryl C1-C6 alkyl, substituted or unsubstituted heteroaryl, substituted or unsubstituted heteroarylC1-C6 alkyl, carbonylC1-C6 alkyl, thiocarbonylC1-C6 alkyl, sulfonylC1-C3 alkyl, sulfinylC1-C6 alkyl, iminoC1-C6 alkyl, —O—C1-C6 alkyl; and R4 is selected from: hydrogen; C1-C6 alkyl optionally substituted by halogen, nitro, cyano; C1-C6 oxygen-containing alkyl; C3-C7 cycloalkyl optionally substituted by halogen, nitro, cyano; —O—C1-C6 alkyl optionally substituted by halogen, nitro, amino, cyano; —O—C3-C7 cycloalkyl optionally substituted by halogen, nitro, amino, cyano; C6-C10 aryl optionally substituted by halogen, nitro, amino, cyano; —O—C6-C10 aryl optionally substituted by halogen, nitro, amino, cyano; C2-C6 alkenyl; C3-C6 acyl; C1-C6 alkylsulfonyl.

In one embodiment, R1 is selected from: hydrogen, halogen, C1-C6 alkyl, C3-C7 cycloalkyl, —O—C1-C6 alkyl, —O—C3-C7 cycloalkyl, C6-C10 aryl Group, —O—C6-C10 aryl, C2-C6 alkenyl.

In another embodiment, R1 is selected from: hydrogen, C1-C3 alkyl, C3-C7 cycloalkyl, halogen.

In another embodiment, R1 is selected from: hydrogen.

In one embodiment, R2 is selected from: hydrogen, halogen, C1-C6 alkyl, C3-C7 cycloalkyl, —O—C1-C6 alkyl, —O—C3-C7 cycloalkyl, C6-C10 aryl Group, —O—C6-C10 aryl, C2-C6 alkenyl.

In another embodiment, more preferably R2 is selected from: hydrogen, C1-C3 alkyl, C3-C7 cycloalkyl, halogen.

In another embodiment, R2 is selected from: hydrogen, methyl.

In one embodiment, R3 is selected from: hydrogen, halogen, nitro, C1-C3 alkyl, C3-C7 cycloalkyl, C3-C7 cycloalkyl, C1-C3 alkyl, heterocyclyl C1-C3 alkyl, C6-C10 aryl, C6-C10 aryl, C1-C3 alkyl, heteroaryl C1-C3 alkyl.

In another embodiment, the above mentioned R3 is at the 2-position.

In another embodiment, R3 is selected from: hydrogen, methyl at 2-position, nitro at 2-position.

In one embodiment, R4 is selected from: hydrogen, C1-C6 alkyl, C3-C7 cycloalkyl, —O—C1-C6 alkyl, —O—C3-C7 cycloalkyl, C6-C10 aryl, —O—C6-C10 aryl, C2-C6 alkenyl, C3-C6 acyl, C1-C6 alkylsulfonyl.

In another embodiment, R4 is selected from: hydrogen, C1-C3 alkyl, C3-C7 cycloalkyl, C3-C6 acyl, C1-C6 alkylsulfonyl.

In another embodiment, R4 is selected from: hydrogen, ethyl, propyl, isopropyl, cyclopropyl, propionyl, and methylsulfonyl.

The Term

Unless otherwise defined, all scientific and technological terms used herein have the same definitions that are generally understood by a person skilled in the art to which the claimed subject matter belongs.

Unless otherwise specified, the present disclosure adopts routine methods such as mass spectrometry (MS), nuclear magnetic resonance (NMR), high performance liquid phase (HPLC), protein chemistry, biochemistry, recombinant DNA technology, and pharmacology within the technical field. Unless specific definitions are provided, the name and laboratory operation techniques related to analytical chemistry, synthetic organic chemistry, and medicine and medicinal chemistry related to this article are known to a person skilled in the art. In general, the aforementioned techniques and steps can be implemented by routine methods well known in the art and described in various general documents and more specific documents, which are cited or discussed in this description.

Unless otherwise specified, the aforementioned groups and substituents have ordinary meanings in the field of medicinal chemistry.

It should be noted that the term "halogen" refers to fluorine, chlorine, bromine or iodine.

The term "nitro" refers to the —$NO_2$ group.

The term "cyano" refers to the —CN group.

The term "hydroxy" refers to the —OH group.

The term "$C_1$-$C_6$ alkyl" refers to any straight chained or branched group containing 1-6 carbon atoms, such as methyl, ethyl, n-propyl, isopropyl, n-butyl, isobutyl, tert-butyl, sec-butyl, n-pentyl, tert-pentyl, n-hexyl, etc.

The term "$C_1$-$C_3$ alkyl" refers to any straight chained or branched group containing 1-3 carbon atoms, such as methyl, ethyl, n-propyl, isopropyl and the like.

The term "C1-C6 oxygen-containing alkyl group" refers to a group formed by replacing the C1-C6 alkyl skeleton with one or more C1-C6 alkoxy groups, for example, methoxyethyl, methoxyethoxymethyl etc.

The term "C3-C7 cycloalkyl" refers to any cyclic ring group containing 3-7 carbon atoms, such as cyclopropyl, methylcyclopropyl, cyclobutyl, methylcyclobutyl, ethyl cyclopropyl, cyclopentyl, methylcyclopentyl, ethylcyclobutyl, cyclohexyl, methylcyclohexyl, ethylcyclopentyl, cycloheptyl, etc.

The term "C2-C6 alkenyl" refers to any straight chained or branched group containing 2-6 carbon atoms and at least one alkenyl group, such as vinyl, allyl, 1-propenyl, isopropenyl, 1-butenyl, 2-butenyl, 3-butenyl, 2-pentenyl, 1-hexenyl and the like.

The term "C6-C10 aryl" refers to a mono-, di- or multi-carbocyclic ring hydrocarbon having 6-10 carbon atoms, which has 1-2 ring systems optionally further fused or connected to each other through single bonds, wherein at least one of the carbon rings is "aromatic", wherein the term "aromatic" refers to a fully conjugated π-electron bond system. The aryl ring may optionally be further fused or connected to aromatic and non-aromatic carbocyclic and heterocyclic rings. Non-limiting examples of the C6-C10 aryl group are phenyl, α- or β-naphthyl.

Similarly, "C9-C12 bicyclic aryl" refers to a mono-, bicyclic hydrocarbon having 9-12 carbon atoms, which has two ring systems optionally further fused or connected to each other through a single bond, wherein at least one of the carbocyclic rings is "aromatic", where the term "aromatic" refers to a fully conjugated π-electron bond system. Non-limiting examples of the C9-C12 bicyclic aryl group are α- or β-naphthyl, α- or β-naphthyl substituted by methyl, ethyl or the like.

The terms "—O—C1-C6 alkyl", "—O—C3-C7 cycloalkyl", and "—O—C6-C10 aryl" refer to any of the aforementioned C1-C6 alkyl, C3-C7 cycloalkanes Group, C6-C10 aryl group, which is connected to the rest of the molecule through an oxygen atom (—O—).

The term "heteroaryl" refers to an aromatic heterocyclic ring, usually a 5- to 8-membered heterocyclic ring having 1 to 3 heteroatoms selected from N, O or S; the heteroaryl ring may optionally be further fused or connected to aromatic and non-aromatic carbocyclic and heterocyclic rings. Non-limiting examples of the heteroaryl group are, for example, pyridyl, pyrazinyl, pyrimidinyl, pyridazinyl, indolyl, imidazolyl, thiazolyl, isothiazolyl, thiaoxazolyl, pyrrolyl, phenyl-pyrrolyl, furanyl, phenyl-furyl, oxazolyl, isoxazolyl, pyrazolyl, thienyl, benzothienyl, isoindolinyl, benzimidazolyl, indazolyl, quinolinyl, isoquinolinyl, 1,2,3-triazolyl, 1-phenyl-1,2,3-triazolyl, 2,3-indoline, 2,3-di hydrobenzofuranyl, 2,3-dihydrobenzothienyl, benzopyranyl, 2,3-dihydrobenzoxazinyl, 2,3-dihydroquinoxalinyl, etc.

The term "heteroC9-C12 bicyclic aryl group" means that the carbon atoms in the above-defined "C9-C12 bicyclic aryl group" are replaced by 1 to 3 heteroatoms selected from N, O or S.

The term "heterocyclyl" (also known as "heterocycloalkyl") refers to 3-, 4-, 5-, 6-, and 7-membered saturated or partially unsaturated carbocyclic rings in which one or more carbon atoms replaced by heteroatoms such as nitrogen, oxygen and sulfur. Non-limiting examples of heterocyclyls are, for example, pyran, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine, tetrahydropyrrolyl, thiomorpholinyl, etc.

The term "C3-C6 acyl" refers to —C(═O)—C2-C5 alkyl, such as propionyl, butyryl, valeryl, hexanoyl and the like.

According to the present disclosure and unless otherwise provided, any of the aforementioned groups may alternatively be substituted at any of its free positions by one or more groups, for example by 1-6 groups which independently selected from: halogen atoms, nitro, oxo (═O), cyano, C1-C6 alkyl, polyfluorinated alkyl, polyfluorinated alkoxy, alkenyl, alkynyl, hydroxylalkyl, hydroxyalkylamino, hydroxyl heterocyclyl, aryl, aryl-alkyl, heteroaryl, heteroaryl-alkyl, heterocyclyl, heterocyclyl-alkyl, C3-C7 cycloalkyl, cycloalkyl-alkyl, alkyl-aryl, alkyl-heteroaryl, alkyl-heteroclyl, alkyl-cycloalkyl, alkyl-aryl-alkyl, alkyl-heteroaryl-alkyl, alkyl-heterocyclyl-alkyl, alkyl-cycloalkyl-alkyl, alkyl-heterocyclyl-heterocyclyl, heterocyclyl-heterocyclyl, heterocyclyl-alkyl-heterocyclyl, heterocyclyl-alkylamino, alkyl-heterocyclyl-alkylamino, hydroxyl, alkoxy, aryloxy, heterocyclyloxyl, alkyl-heterocyclyloxyl, methylenedioxy, alkylcarbonyloxy, arylcarbonyloxy, cycloalkenyloxy, heterocyclylcarbonyloxy, alkyleneaminooxy, carboxyl, alkoxycarbonyl, aryloxycarbonyl, cycloalkyloxycarbonyl, heterocyclyl oxycarbonyl, amino, ureido, alkyl amino, amino-alkylamino, dialkylamino, dialkylamino-heterocyclyl, dialkylamino-alkylamino, arylamino, arylalkylamino, diarylamino, heterocyclylamino, alkyl-heterocyclylamino, alkyl-heterocyclylcarbonyl, carbonylamino, alkylcarbonylamino, arylcarbonylamino, heterocyclylcarbonylamino, alkyl-heterocyclylcarbonylamino, aminocarbonyl, alkylaminocarbonyl, dialkylaminocarbonyl, arylaminocarbonyl, heterocyclylaminocarbonyl, alkoxycarbonylamino, alkoxycarbonylamino-alkylamino, alkoxyalkylcarbonylheterocyclyl-alkylamino, alkoxy-aryl-alkyl, hydroxylamino-carbonyl, alkoxyimino, alkylsulfonylamino, arylsulfonylamido, heterocyclylsulfonylamido, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

From all the descriptions above, it is obvious to a person skilled in the art that any group of which the name is a compound name, such as "C1-C6 alkylsulfonyl", should refer to the part routinely derived therefrom, such as from C1-C6alkyl substituted sulfonyl, wherein C1-C6 alkyl is as defined above.

Similarly, any terms such as C3-C7cycloalkyl C1-C6 alkyl, C3-C7cycloalkyl C1-C3 alkyl, heteroC3-C7 cycloalkyl C1-C6 alkyl, heteroC3-C7 cycloalkyl C1-C3 alkyl, hetero C4-C12 bicyclic aryl C1-C3 alkyl, C6-C10 aryl C1-C3 alkyl, C6-C10 aryl C1-C6 alkyl, heteroaryl C1-C6 alkyl, carbonyl C1-C6 alkyl, thiocarbonyl C1-C6 alkyl, sulfonyl C1-C3 alkyl, sulfinyl C1-C6 alkyl, imino C1-C6 alkyl, heteroaryl C1-C3 alkyl, wherein the respective parts constituting the combined group are as defined above.

For each variable, any combination of the above groups is also considered in the present disclosure. It is understood that the substituents and substitution patterns on the compounds provided herein can be selected by a person skilled in the art in order to provide chemically stable other compounds synthesized using techniques known in the art as well as the techniques described herein can be used.

As used herein, unless otherwise specified, the term "pro-drug" refers to a derivative that can be hydrolyzed, oxidized, or otherwise reacted under biological conditions (in vitro or in vivo) to provide a compound of the disclosure. Pro-drugs only undergo this reaction under biological conditions to become active compounds, or they are active in their unreactive form. The pro-drugs can generally be prepared using well-known methods, such as those described in 1 Burger's Medicinal Chemistry and Drug Discovery (1995) 172-178, 949-982 (Manfred E. Wolff Ed., 5th edition).

As used herein, examples of the term "pharmaceutically acceptable salts of compounds of formula (I)" are organic acid addition salts formed from organic acids that form pharmaceutically acceptable anions, including but not limited to formate, acetate, propionate, benzoate, maleate, fumarate, succinate, tartrate, citrate, ascorbate, α-ketoglutarate, α-glycerophosphate, alkyl sulfonate or aryl sulfonate; preferably, the alkyl sulfonate is methyl sulfonate or ethyl sulfonate; the aryl sulfonate is phenyl sulfonate or p-toluenesulfonate. Suitable inorganic salts can also be formed, including but not limited to hydrochloride, hydrobromide, hydroiodide, nitrate, bicarbonate and carbonate, sulfate or phosphate, and the like.

Pharmaceutically acceptable salts can be obtained using standard procedures well known in the art, for example, by reacting a sufficient amount of a basic compound with a suitable acid that provides a pharmaceutically acceptable anion.

Further embodiments of the compound of Formula (I) include but not limited to compounds selected from the following:
1-(4-(4-Methyl-6-oxo-1,4,5,6-tetrahydropyridazine-3-yl)phenyl)guanidine
N—(N-(4-(4-Methyl-6-oxo-1,4,5,6-tetrahydropyridazine-3-yl)phenyl) amidino)propionamide
1-ethyl-3-(4-(4-methyl-6-oxo-1,4,5,6-tetrahydropyridazine-3-yl)phenyl)guanidine
1-(4-(4-Methyl-6-oxo-1,4,5,6-tetrahydropyridazine-3-yl)phenyl)-3-propylguanidine
1-isopropyl-3-(4-(4-methyl-6-oxo-1,4,5,6-tetrahydropyridazine-3-yl)phenyl)guanidine
1-cyclopropyl-3-(4-(4-methyl-6-oxo-1,4,5,6-tetrahydropyridazine-3-yl)phenyl)guanidine
N—(N-(4-(4-Methyl-6-oxo-1,4,5,6-tetrahydropyridazine-3-yl)phenyl) amidino)methanesulfonamide
1-(4-(6-oxo-1,4,5,6-tetrahydropyridazine-3-yl)phenyl)guanidine
N—(N-(4-(6-oxo-1,4,5,6-tetrahydropyridazine-3-yl)phenyl)amidino)propionamide
1-ethyl-3-(4-(6-oxo-1,4,5,6-tetrahydropyridazine-3-yl)phenyl)guanidine
1-(4-(6-oxo-1,4,5,6-tetrahydropyridazine-3-yl)phenyl)-3-propylguanidine
1-isopropyl-3-(4-(6-oxo-1,4,5,6-tetrahydropyridazine-3-yl)phenyl)guanidine
1-cyclopropyl-3-(4-(6-oxo-1,4,5,6-tetrahydropyridazine-3-yl)phenyl)guanidine
N—(N-(4-(6-oxo-1,4,5,6-tetrahydropyridazine-3-yl)phenyl)amidino)methanesulfonamide
1-(4-(4-methyl-6-oxo-1,4,5,6-tetrahydropyridazine-3-yl)-2-nitrophenyl)guanidine
N—(N-(4-(4-Methyl-6-oxo-1,4,5,6-tetrahydropyridazine-3-yl)-2-nitrophenyl)amidino)propionamide
1-ethyl-3-(4-(4-methyl-6-oxo-1,4,5,6-tetrahydropyridazine-3-yl)-2-nitrophenyl)guanidine
1-(4-(4-Methyl-6-oxo-1,4,5,6-tetrahydropyridazine-3-yl)-2-nitrophenyl)-3-propylguanidine
1-isopropyl-3-(4-(4-methyl-6-oxo-1,4,5,6-tetrahydropyridazine-3-yl)-2-nitrophenyl)guanidine
1-cyclopropyl-3-(4-(4-methyl-6-oxo-1,4,5,6-tetrahydropyridazine-3-yl)-2-nitrophenyl)guanidine
N—(N-(4-(4-Methyl-6-oxo-1,4,5,6-tetrahydropyridazin-3-yl)-2-nitrophenyl)carboxamidino)methanesulfon Amide
1-(2-methyl-4-(4-methyl-6-oxo-1,4,5,6-tetrahydropyridazine-3-yl)phenyl)guanidine
N—(N-(2-methyl-4-(4-methyl-6-oxo-1,4,5,6-tetrahydropyridazine-3-yl)phenyl)amidino)propionamide
1-ethyl-3-(2-methyl-4-(4-methyl-6-oxo-1,4,5,6-tetrahydropyridazine-3-yl)phenyl)guanidine
1-(2-Methyl-4-(4-methyl-6-oxo-1,4,5,6-tetrahydropyridazine-3-yl)phenyl)-3-propylguanidine
1-isopropyl-3-(2-methyl-4-(4-methyl-6-oxo-1,4,5,6-tetrahydropyridazine-3-yl)phenyl)guanidine
1-cyclopropyl-3-(2-methyl-4-(4-methyl-6-oxo-1,4,5,6-tetrahydropyridazine-3-yl)phenyl)guanidine
N—(N-(2-methyl-4-(4-methyl-6-oxo-1,4,5,6-tetrahydropyridazine-3-yl)phenyl)amidino)methanesulfonamide.

The pharmaceutical composition of the present disclosure

The application also provides a pharmaceutical composition, wherein contains at least one compound of Formula (I) or a pharmaceutically acceptable salt, solvate, ester, acid, pharmaceutically active metabolite or pro-drug of the compound, and pharmaceutically acceptable carriers or excipients, and optionally other therapeutic agents.

In the treatment, the compound can be used alone or in combination with one or more other therapeutic agents according to the situation. The drug containing the compound of the present disclosure can be administered to the patient by at least one of injection, oral administration, inhalation, rectal or transdermal administration. Other therapeutic agents can be selected from the following drugs:
1-(4-(4-Methyl-6-oxo-1,4,5,6-tetrahydropyridazine-3-yl)phenyl)guanidine
N—(N-(4-(4-Methyl-6-oxo-1,4,5,6-tetrahydropyridazine-3-yl)phenyl) amidino)propionamide
1-ethyl-3-(4-(4-methyl-6-oxo-1,4,5,6-tetrahydropyridazine-3-yl)phenyl)guanidine 1-(4-(4-Methyl-6-oxo-1,4,5,6-tetrahydropyridazine-3-yl) phenyl)-3-propylguanidine
1-isopropyl-3-(4-(4-methyl-6-oxo-1,4,5,6-tetrahydropyridazine-3-yl)phenyl)guanidine
1-cyclopropyl-3-(4-(4-methyl-6-oxo-1,4,5,6-tetrahydropyridazine-3-yl)phenyl)guanidine
N—(N-(4-(4-Methyl-6-oxo-1,4,5,6-tetrahydropyridazine-3-yl)phenyl) amidino)methanesulfonamide
1-(4-(6-oxo-1,4,5,6-tetrahydropyridazine-3-yl)phenyl)guanidine
N—(N-(4-(6-oxo-1,4,5,6-tetrahydropyridazine-3-yl)phenyl)amidino)propionamide
1-ethyl-3-(4-(6-oxo-1,4,5,6-tetrahydropyridazine-3-yl)phenyl)guanidine
1-(4-(6-oxo-1,4,5,6-tetrahydropyridazine-3-yl)phenyl)-3-propylguanidine
1-isopropyl-3-(4-(6-oxo-1,4,5,6-tetrahydropyridazine-3-yl)phenyl)guanidine
1-cyclopropyl-3-(4-(6-oxo-1,4,5,6-tetrahydropyridazine-3-yl)phenyl)guanidine
N—(N-(4-(6-oxo-1,4,5,6-tetrahydropyridazine-3-yl)phenyl) amidino)methanesulfonamide
1-(4-(4-methyl-6-oxo-1,4,5,6-tetrahydropyridazine-3-yl)-2-nitrophenyl)guanidine
N—(N-(4-(4-methyl-6-oxo-1,4,5,6-tetrahydropyridazine-3-yl)-2-nitrophenyl)carboxamidino)propionamide
1-ethyl-3-(4-(4-methyl-6-oxo-1,4,5,6-tetrahydropyridazine-3-yl)-2-nitrophenyl)guanidine
1-(4-(4-Methyl-6-oxo-1,4,5,6-tetrahydropyridazine-3-yl)-2-nitrophenyl)-3-propylguanidine1-isopropyl-3-(4-(4-methyl-6-oxo-1,4,5,6-tetrahydropyridazine-3-yl)-2-nitrophenyl)guanidine
1-cyclopropyl-3-(4-(4-methyl-6-oxo-1,4,5,6-tetrahydropyridazine-3-yl)-2-nitrophenyl)guanidine
N—(N-(4-(4-methyl-6-oxo-1,4,5,6-tetrahydropyridazine-3-yl)-2-nitrophenyl) amidino)methanesulfon amide
1-(2-methyl-4-(4-methyl-6-oxo-1,4,5,6-tetrahydropyridazine-3-yl)phenyl)guanidine
N—(N-(2-methyl-4-(4-methyl-6-oxo-1,4,5,6-tetrahydropyridazine-3-yl)phenyl) amidino)propionamide
1-ethyl-3-(2-methyl-4-(4-methyl-6-oxo-1,4,5,6-tetrahydropyridazine-3-yl)phenyl)guanidine;
1-(2-methyl-4-(4-methyl-6-oxo-1,4,5,6-tetrahydropyridazine-3-yl)phenyl)-3-propylguanidine
1-isopropyl-3-(2-methyl-4-(4-methyl-6-oxo-1,4,5,6-tetrahydropyridazine-3-yl)phenyl)guanidine
1-cyclopropyl-3-(2-methyl-4-(4-methyl-6-oxo-1,4,5,6-tetrahydropyridazine-3-yl)phenyl)guanidine
N—(N-(2-methyl-4-(4-methyl-6-oxo-1,4,5,6-tetrahydropyridazine-3-yl)phenyl) amidino)methanesulfonamide.

In the embodiments of the present disclosure, when a patient is treated according to the present disclosure, the amount of drug administered depends on many factors, such as the specific dosing regimen, the type of disease or condition and its severity, the subject to be treated or the host's uniqueness (such as body weight), but, according to specific surrounding conditions, including, for example, the specific used drug, the route of administration, the condition to be treated, and the subject or host to be treated, the dosage can be routinely determined by methods known in the art. Generally, in terms of the dosage used for adult treatment, the administered dosage is typically 0.1 mg-5000 mg/day, and the preferred dosage is: 10 mg-500 mg/day. The required dosage can be conveniently expressed as one dose or simultaneously administered (or within a short period of time) or divided doses at appropriate intervals, such as 2, 3, 4 or more divided doses per day. A person skilled in the art can understand that although the above-mentioned dosage range is given, the specific effective amount can be appropriately adjusted according to the patient's condition and in conjunction with the doctor's diagnosis.

The compounds of formula (I) are used as P2Y12 receptor antagonists and can be used to treat cardiovascular and cerebrovascular diseases, especially thromboembolic diseases, including but not limited to inhibitors of platelet activation, platelet aggregation and platelet degranulation, and used as a promoter of platelet depolymerization and an antithrombotic agent. The compound of the present application is also used to treat or prevent unstable angina pectoris (coronary heart disease), percutaneous transluminal coronary angioplasty (PCTA), myocardial infarction, peripheral thrombolysis, atherosclerotic thrombotic arterial complications, etc.

The use of the compounds of present application in preventing and/or treating the above-mentioned diseases and the use in preparing medicines for the treatment of these diseases are within the scope of the present application.

Compound Preparation

The compound of Formula (I) can be synthesized according to standard synthesis techniques known to a person skilled in the art or methods known in the art in combination with the methods described in this patent. In addition, the solvent, temperature and other reaction conditions given herein can be changed according to the skill in the art. As further guidance, the following synthesis methods can also be used.

In some embodiments, provided herein are the preparation methods and methods of using the pyridazinone compounds described herein. In some embodiments, the compounds described herein can be synthesized using the following synthesis scheme. A method similar to that described below can be used to synthesize the compound by using appropriate optional starting materials.

The starting materials used to synthesize the compounds described herein can be synthesized or can be obtained from commercial sources. The compounds described herein and other related compounds with different substituents can be synthesized using techniques and raw materials known to those skilled in the art. The general methods for preparing the compounds disclosed herein can be derived from reactions known in the art, and the reactions can be modified by reagents and conditions deemed appropriate by a person skilled in the art to introduce various moieties in the molecules provided herein.

If necessary, the reaction products can be separated and purified with conventional techniques, including but not limited to methods such as filtration, distillation, crystallization, and chromatography. These products can be characterized by using conventional methods, including physical constants and spectral data.

General Synthetic Scheme of Formula (1):

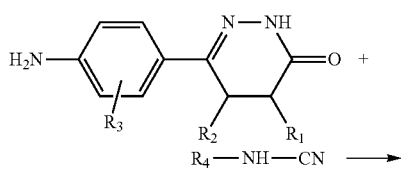

-continued

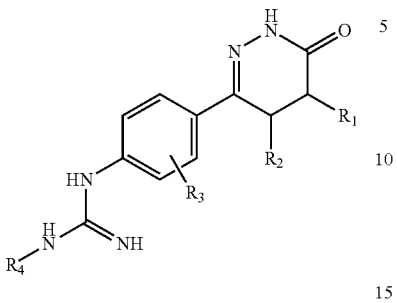

Reaction conditions: the compound (1) is dissolved in a solvent, the solvent can be selected from methanol, ethanol, acetone, etc.; glacial acetic acid and (2) aqueous solution are added dropwise in sequence, the reaction is heated and refluxed for 4-12 hours, and the solvent is concentrated under reduced pressure, add water, adjust the pH to about 12~13 with anhydrous sodium carbonate, and filter with suction to obtain the corresponding compound.

EXAMPLES

The following specific non-limiting examples will be construed as merely illustrative and do not limit the present disclosure in any way. Although no further detailed description is required, it is believed that those skilled in the art can fully utilize the present disclosure based on the description herein.

Example 1 Synthesis of 6-(4-aminophenyl)-5-methyl-4,5-dihydropyridazine-3(2H)-one

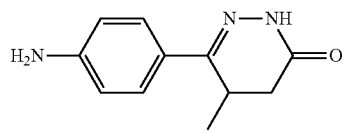

30 kg of 10% ethanol solution, 4-(4-aminophenyl)-3-methyl-4-oxobutyric acid (Chengdu Yuancheng Biotechnology Co., Ltd.) 9.0 kg and hydrazine hydrate 4.95 kg/kg were added in a reaction flask in sequence and the reaction mixture was heated to 80° C.±5° C. to reflux for 5 h. The reaction was stopped and cooled to room temperature, and was crystallized for 12 h, with light yellow solid precipitates. After filtering, the filter cake was dried at 80-85° C. to obtain 5.2 kg of 6-(4-aminophenyl)-5-methyl-4,5-dihydropyridazine-3(2H)-one.

$^1$H NMR (400 MHz, DMSO-d6) δ10.64 (s, 1H), 7.46~7.75 (m, 2H), 6.56~6.61 (m, 2H), 5.49 (s, 2H), 3.24~3.31 (m, 1H), 2.56~2.62 (m, 1H), 2.14~2.19 (m, 1H), 1.03~1.08 (m, 3H); Molecular Formula: $C_{11}H_{13}N_3O$, Molecular Weight: 203.2, MS (m/z): 204.1.

Example 2

Synthesis of 1-(4-(4-methyl-6-oxo-1,4,5,6-tetrahydropyridazin-3-yl)phenyl)guanidine

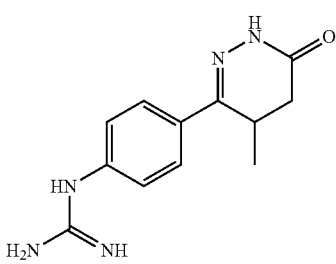 [SMILES: CC1CC(=O)NN=C1c1ccc(NC(=N)N)cc1]

The reaction mixture of 6-(4-Aminophenyl)-5-methyl-4,5-dihydropyridazine-3(2H)-one 200 g, 1.5 L absolute ethanol was add 130 ml glacial acetic acid and 240 ml of 50% cyanamide aqueous solution dropwise with stirring. After dropping completed, the reaction was basically completed after the temperature was raised to reflux for 5 h. The ethanol was concentrated under reduced pressure, 2 L of water was added, and the pH was adjusted to about 12~13 with anhydrous sodium carbonate while temperature was at room temperature, and then filtered with suction. The filter cake was recrystallized from ethanol to obtain 1-(4-(4-methyl-6-oxo-1,4,5,6-tetrahydropyridazin-3-yl)phenyl)guanidine.

$^1$H NMR (400 MHz, DMSO-d6) δ11.64 (s, 2H), 11.45 (s, 1H), 7.83~7.81 (d, J=8.0 Hz, 2H), 6.54~6.52 (d, J=8.0 Hz, 2H), 5.48 (s, 1H), 3.73~3.39 (m, 1H), 2.77~2.58 (m, 1H), 1.87~1.54 (m, 1H), 1.10~1.05 (m, 3H); Molecular Formula: $C_{12}H_{15}N_5O$, Molecular weight: 245.3, MS (m/z): 246.7.

Example 3

Synthesis of N—(N-(4-(4-methyl-6-oxo-1,4,5,6-tetrahydropyridazin-3-yl)phenyl)carboxamidino)propionamide

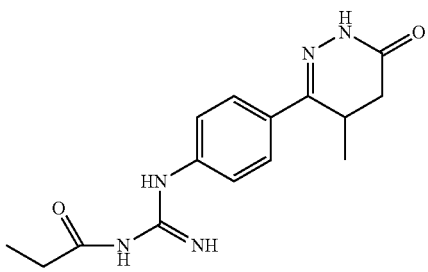 [SMILES: CCC(=O)NC(=N)Nc1ccc(C2=NNC(=O)CC2C)cc1]

Cyanamide in Example 2 was replaced by N-cyanopropionamide, and the above compound was obtained according to the preparing method described in Examples 1 and 2.

$^1$H NMR (400 MHz, DMSO-d6) δ11.06 (s, 1H), 10.21 (s, 1H), 7.58~7.57 (d, J=7.6 Hz, 2H), 6.71~6.69 (d, J=7.6 Hz, 2H), 5.27 (s, 1H), 2.44~2.39 (m, 4H), 1.73~1.59 (m, 1H), 1.22~1.20 (t, J=7.2 Hz, 3H), 0.9~90.92 (m, 3H); Molecular Formula: $C_{15}H_9N_5O_2$, Molecular Weight: 301.3, MS (m/z): 302.4.

Example 4

1-ethyl-3-(4-(4-methyl-6-oxo-1,4,5,6-tetrahydropyridazin-3-yl)phenyl)guanidine

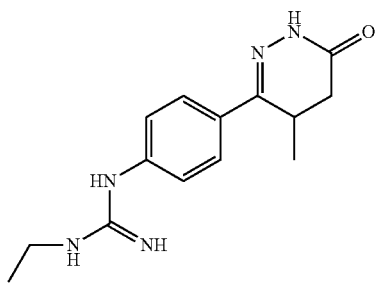 [SMILES: CCNC(=N)Nc1ccc(C2=NNC(=O)CC2C)cc1]

Monocyanamide in Example 2 was replaced by cyanoethylamine, and the synthesis method was referred to Examples 1 and 2.

$^1$H NMR (400 MHz, DMSO-d6) δ10.57 (s, 1H), 7.73~7.71 (d, J=8.0 Hz, 2H), 6.57~6.55 (d, J=8.0 Hz, 2H), 4.58 (s, 1H), 2.72~2.70 (q, J=7.2 Hz, 2H), 2.38~2.21 (m, 2H), 1.70~1.59 (m, 1H), 0.9~90.92 (m, 3H), 0.81~0.79 (t, J=7.2 Hz, 3H); Molecular Formula: $C_{14}H_{19}N_5O$, Molecular Weight: 273.3, MS (m/z): 274.2.

Example 5

1-(4-(4-methyl-6-oxo-1,4,5,6-tetrahydropyridazin-3-yl)phenyl)-3-propylguanidine

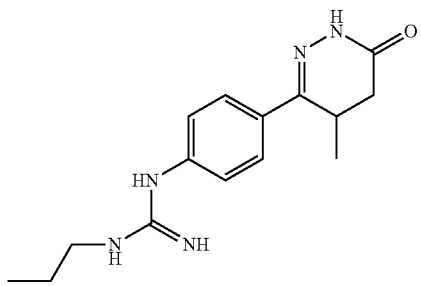 [SMILES: CCCNC(=N)Nc1ccc(C2=NNC(=O)CC2C)cc1]

Cyanamide in Example 2 was replaced by cyanopropylamine, and the synthesis method was referred to Examples 1 and 2.

$^1$H NMR (400 MHz, DMSO-d6) δ10.88 (s, 1H), 7.62~7.60 (d, J=8.0 Hz, 2H), 6.38~6.36 (d, J=8.0 Hz, 2H), 4.11 (s, 1H), 2.87~2.85 (q, J=7.2 Hz, 2H), 2.33~2.15 (m, 2H), 1.66~1.57 (m, 3H), 0.9~40.73 (m, 6H); Molecular Formula: $C_5H_{21}N_5O$, Molecular Weight: 287.4, MS (m/z): 288.6.

Example 6

1-isopropyl-3-(4-(4-methyl-6-oxo-1,4,5,6-tetrahydropyridazin-3-yl)phenyl)guanidine

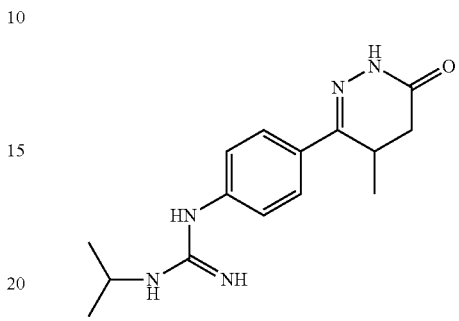

monocyanamide in Example 2 was replaced by N-isopropyl cyanamide, and the synthesis method was referred to Examples 1 and 2.

$^1$H NMR (400 MHz, DMSO-d6) δ10.37 (s, 1H), 7.66~7.64 (d, J=7.6 Hz, 2H), 6.47~6.45 (d, J=7.6 Hz, 2H), 4.39 (s, 1H), 3.39 (m, 1H), 2.47~2.38 ((m, 1H), 2.26~2.15 (m, 1H), 1.59~1.53 (m, 1H), 1.11~1.04 (s, 6H), 0.98~0.88 (m, 3H); Molecular Formula: $C_{15}H_{21}N_5O$, Molecular Weight: 287.4, MS (m/z): 288.5.

Example 7

1-cyclopropyl-3-(4-(4-methyl-6-oxo-1,4,5,6-tetrahydropyridazin-3-yl)phenyl)guanidine

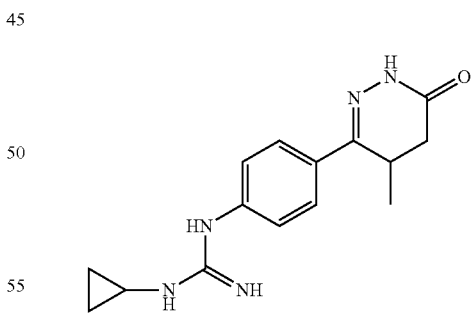

The cyanamide in Example 2 was replaced by N-cyclopropyl cyanamide, and the synthesis method was referred to Examples 1 and 2.

$^1$H NMR (400 MHz, DMSO-d6) δ10.82 (s, 1H), 7.83~7.81 (d, J=8.0 Hz, 2H), 6.86~6.84 (d, J=8.0 Hz, 2H), 4.44 (s, 1H), 2.39~2.24 ((m, 2H), 1.86~1.72 (m, 2H), 0.91~0.76 (m, 7H); Molecular Formula: $C_{15}H_{19}N_5O$, Molecular Weight: 285.3, MS (m/z): 286.3.

Example 8

N—(N-(4-(4-Methyl-6-oxo-1,4,5,6-tetrahydropyridazin-3-yl)phenyl)carboxamidino)methanesulfonamide

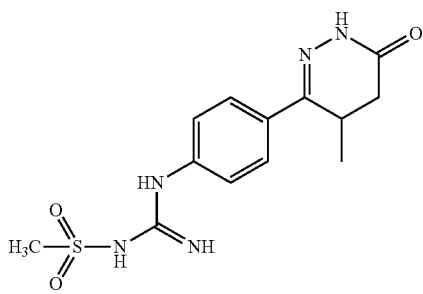 [SMILES: CC1CC(=O)NN=C1c1ccc(NC(=N)NS(C)(=O)=O)cc1]

The monocyanamide in Example 2 was replaced by N-cyanomethylsulfonamide, and the synthesis method was referred to Examples 1 and 2. ¹H NMR (400 MHz, DMSO-d6) δ11.01 (s, 1H), 8.12~8.10 (d, J=8.0 Hz, 2H), 6.88~6.86 (d, J=8.0 Hz, 2H), 4.39 (s, 1H), 3.17 (s, 1H), 2.47~2.33 (m, 1H), 2.21~2.15 (m, 1H), 1.57~1.43 (m, 1H), 0.92 (m, 3H); Molecular Formula: $C_{13}H_{17}N_5O_3S$, Molecular Weight: 328.4, MS (m/z): 329.7.

Example 9

Synthesis of 1-(4-(6-oxo-1,4,5,6-tetrahydropyridazin-3-yl)phenyl)guanidine

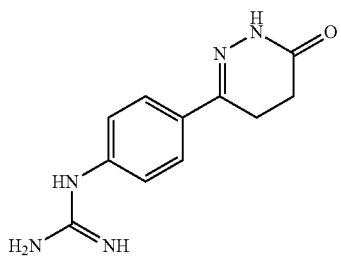

(1) Synthesis of 6-(4-aminophenyl)-4,5-dihydropyridazine-3(2H)-one 4-(4-aminophenyl)-3-methyl-4-oxobutanoic acid in Example 1 was replaced by 4-(4-aminophenyl)-4-oxobutanoic acid (Reference J ENZYM INHIB MED CH, 28(6), 1274-1290, 2013 preparation), the synthesis method was referred to Example 1.

(2) Synthesis of 1-(4-(6-oxo-1,4,5,6-tetrahydropyridazin-3-yl)phenyl)guanidine 6-(4-aminophenyl)-4,5-dihydropyridazine-3(2H)-one and cyanamide were used as raw materials, and the synthesis method was referred to Example 2.

¹H NMR (400 MHz, DMSO-d6) δ10.56 (s, 2H), 10.11 (s, 1H), 7.58~7.56 (d, J=8.0 Hz, 2H), 6.67~6.65 (d, J=8.0 Hz, 2H), 4.38 (s, 1H), 3.03~2.92 (m, 2H), 2.47~2.31 (m, 2H); Molecular Formula: $C_{11}H_{13}N_5O$, Molecular Weight: 231.3, MS (m/z): 232.1.

Example 10

N—(N-(4-(6-oxo-1,4,5,6-tetrahydropyridazin-3-yl)phenyl)carboxamidino)propionamide

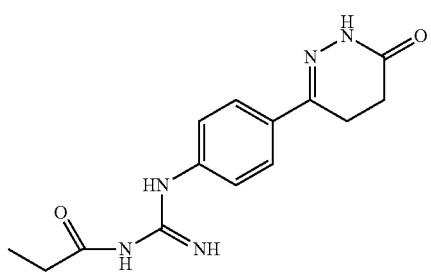 [SMILES: CCC(=O)NC(=N)Nc1ccc(C2=NNC(=O)CC2)cc1]

N-cyanopropionamide and 6-(4-aminophenyl)-4,5-dihydropyridazine-3(2H)-one were used as raw materials, and the synthesis method was referred to Example 2.

¹H NMR (400 MHz, DMSO-d6) δ11.12 (s, 1H), 10.07 (s, 1H), 7.66~7.62 (d, J=8.0 Hz, 2H), 6.59~6.55 (d, J=8.0 Hz, 2H), 5.00 (s, 1H), 2.94~2.83 (m, 2H), 2.73~2.57 (m, 2H), 2.21~2.17 (q, J=7.2 Hz, 2H), 0.99~0.95 (t, J=7.2 Hz, 3H); Molecular Formula: $C_{14}H_{17}N_5O_2$, Molecular Weight: 287.3, MS (m/z): 287.5.

Example 11

Synthesis of 1-ethyl-3-(4-(6-oxo-1,4,5,6-tetrahydropyridazin-3-yl)phenyl)guanidine

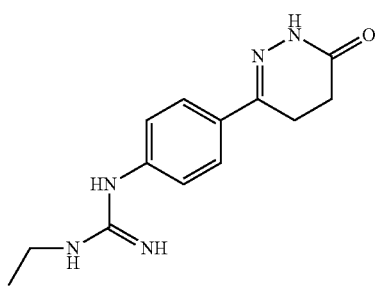 [SMILES: CCNC(=N)Nc1ccc(C2=NNC(=O)CC2)cc1]

Cyanoethylamine and 6-(4-aminophenyl)-4,5-dihydropyridazine-3(2H)-one were used as raw materials, and the synthesis method was referred to Example 2.

¹H NMR (400 MHz, DMSO-d6) δ10.99 (s, 1H), 10.57 (s, 1H), 7.70~7.68 (d, J=8.0 Hz, 2H), 6.81~6.79 (d, J=8.0 Hz, 2H), 5.19 (s, 1H), 2.72~2.70 (q, J=7.2 Hz, 2H), 2.57~2.52 (m, 2H), 2.3~2.21 (m, 2H), 0.81~0.79 (t, J=7.2 Hz, 3H); Molecular Formula: $C_{13}H_{17}N_5O$, Molecular Weight: 259.3, MS (m/z): 260.2.

Example 12

Synthesis of 1-(4-(6-oxo-1,4,5,6-tetrahydro-pyridazin-3-yl)phenyl)-3-propyl guanidine

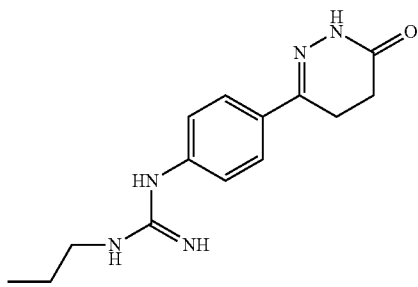 [SMILES: CCCNC(=N)Nc1ccc(C2=NNC(=O)CC2)cc1]

Cyanopropylamine and 6-(4-aminophenyl)-4,5-dihydro-pyridazine-3(2H)-one were used as raw materials, and the synthesis method was referred to Example 2.

$^1$H NMR (400 MHz, DMSO-d6) δ11.00 (s, 1H), 10.61 (s, 1H), 7.78~7.76 (d, J=8.0 Hz, 2H), 6.67~6.65 (d, J=8.0 Hz, 2H), 4.74 (s, 1H), 2.88~2.81 (m, 2H), 2.67~2.64 (q, J=7.2 Hz, 2H), 2.4~12.39 (m, 2H), 1.49~1.33 (m, 2H), 0.81~0.79 (t, J=7.2 Hz, 3H); Molecular Formula: $C_{14}H_{19}N_5O$, Molecular Weight: 273.3, MS (m/z): 274.6.

Example 13

Synthesis of 1-isopropyl-3-(4-(6-oxo-1,4,5,6-tetra-hydropyridazin-3-yl)phenyl)guanidine

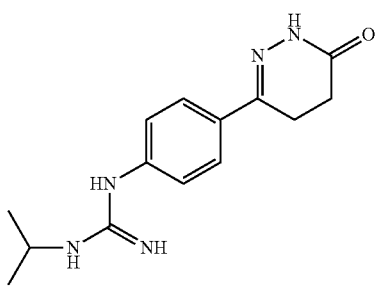 [SMILES: CC(C)NC(=N)Nc1ccc(C2=NNC(=O)CC2)cc1]

N-isopropylcyanamide and 6-(4-aminophenyl)-4,5-dihydropyridazine-3(2H)-one were used as raw materials, and the synthesis method was referred to Example 2.

$^1$H NMR (400 MHz, DMSO-d6) δ11.01 (s, 1H), 10.58 (s, 1H), 7.80~7.78 (d, J=8.0 Hz, 2H), 6.54~6.52 (d, J=8.0 Hz, 2H), 4.97 (s, 1H), 2.99~2.73 (m, 3H), 2.58~2.52 (m, 2H), 1.29~1.22 (m, 6H); Molecular Formula: $C_{14}H_{19}N_5O$, Molecular Weight: 273.3, MS (m/z): 274.6.

Example 14

Synthesis of 1-cyclopropyl-3-(4-(6-oxo-1,4,5,6-tetrahydropyridazin-3-yl)phenyl)guanidine

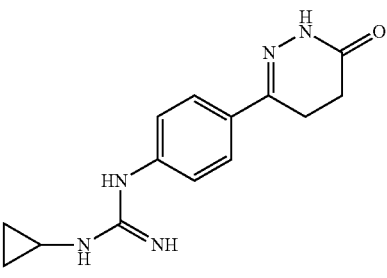 [SMILES: N=C(Nc1ccc(C2=NNC(=O)CC2)cc1)NC1CC1]

N-cyclopropyl cyanamide and 6-(4-aminophenyl)-4,5-dihydropyridazine-3(2H)-one were used as raw materials, and the synthesis method was referred to Example 2.

$^1$H NMR (400 MHz, DMSO-d6) δ10.84 (s, 1H), 10.21 (s, 1H), 7.60~7.58 (d, J=8.0 Hz, 2H), 6.31~6.29 (d, J=8.0 Hz, 2H), 4.55 (s, 1H), 2.79~2.71 (m, 2H), 2.51~2.45 (m, 2H), 1.74~1.51 (m, 1H), 0.87~0.66 (m, 4H); Molecular Formula: $C_{14}H_{17}N_5O$, Molecular Weight: 271.3, MS (m/z): 271.3.

Example 15

Synthesis of N—(N-(4-(6-oxo-1,4,5,6-tetrahydro-pyridazin-3-yl)phenyl)carboxamidino)methanesulfonamide

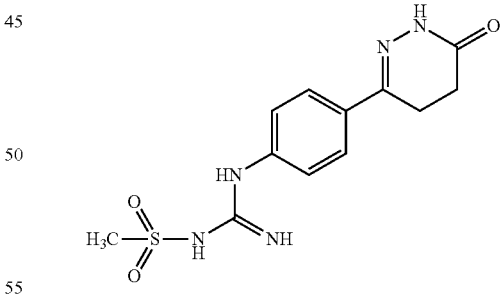

N-cyanomethylsulfonamide and 6-(4-aminophenyl)-4,5-dihydropyridazine-3(2H)-one were used as raw materials, and the synthesis method was referred to Example 2.

$^1$H NMR (400 MHz, DMSO-d6) δ11.21 (s, 1H), 10.35 (s, 1H), 7.81~7.79 (d, J=8.0 Hz, 2H), 6.58~6.56 (d, J=8.0 Hz, 2H), 4.68 (s, 1H), 2.94~2.77 (m, 5H), 2.53~2.40 (m, 2H); Molecular Formula: $C_{12}H_{15}N_5O_3S$, Molecular Weight: 309.3, MS (m/z): 310.7.

Example 16

Synthesis of 1-(4-(4-methyl-6-oxo-1,4,5,6-tetrahydropyridazin-3-yl)-2-nitrophenyl)guanidine

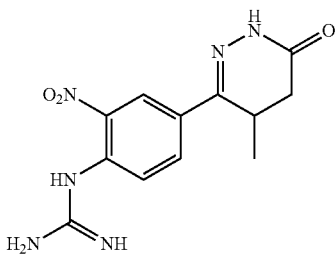 [SMILES: CC1CC(=O)NN=C1c1ccc(NC(=N)N)c([N+](=O)[O-])c1]

1) Synthesis of 6-(4-amino-3-nitrophenyl)-5-methyl 4,5-dihydropyridazine-3(2H)-one 4-(4-aminophenyl)-3-methyl-4-oxobutanoic acid in Example 1 was replaced by 4-(4-amino-3-nitrophenyl)-4-oxobutanoic acid (synthesized by the method of reference INP 2011CH01593), and the synthesis method was referred to Example 1.

(2) The synthesis of 1-(4-(4-methyl-6-oxo-1,4,5,6-tetrahydropyridazin-3-yl)-2-nitrophenyl)guanidine, 6-(4-Amino-3-nitrophenyl)-5-methyl 4,5-dihydropyridazine-3 (2H)-one and cyanamide were used as raw materials, and the synthesis method was referred to Example 2.

$^1$H NMR (400 MHz, DMSO-d6) δ10.81 (s, 2H), 10.33 (s, 1H), 8.46 (s, 1H), 8.05~8.03 (dd, J=8.0 Hz, 1H), 7.08~7.06 (d, J=8.0 Hz, 1H), 4.13 (s, 1H), 2.73~2.39 (m, 1H), 2.27~2.18 (m, 1H), 1.8~11.57 (m, 1H), 1.07~0.95 (m, 3H); Molecular Formula: $C_{12}H_{14}N_6O_3$, Molecular Weight: 290.3, MS (m/z): 291.5.

Example 17

Synthesis of N—(N-(4-(4-Methyl-6-oxo-1,4,5,6-tetrahydropyridazin-3-yl)-2-nitrophenyl)carboxamidino) propionamide

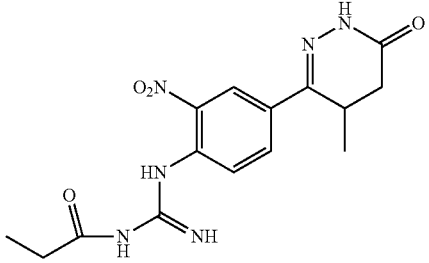 [SMILES: CCC(=O)NC(=N)Nc1ccc(C2=NNC(=O)CC2C)cc1[N+](=O)[O-]]

N-cyanopropionamide and 6-(4-amino-3-nitrophenyl)-5-methyl 4,5-dihydropyridazine-3(2H)-one were used as raw materials, and the synthesis method was referred to Example 2.

$^1$H NMR (400 MHz, DMSO-d6) δ10.88 (s, 2H), 10.54 (s, 1H), 8.23 (s, 1H), 8.01~7.99 (dd, J=8.0 Hz, 1H), 7.35~7.33 (d, J=8.0 Hz, 1H), 4.72 (s, 1H), 2.59~2.37 (m, 4H), 2.24~2.19 (m, 1H), 1.0~70.95 (m, 6H); Molecular Formula: $C_{15}H_{18}N_6O_4$, Molecular Weight: 346.3, MS (m/z): 347.2.

Example 18

Synthesis of 1-ethyl-3-(4-(4-methyl-6-oxo-1,4,5,6-tetrahydropyridazin-3-yl)-2-nitrophenyl)guanidine

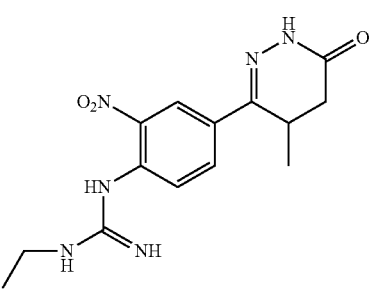 [SMILES: CCNC(=N)Nc1ccc(C2=NNC(=O)CC2C)cc1[N+](=O)[O-]]

Cyanoethylamine and 6-(4-amino-3-nitrophenyl)-5-methyl 4,5-dihydropyridazine-3(2H)-one were used as raw materials, and the synthesis method was referred to Example 2.

$^1$H NMR (400 MHz, DMSO-d6) δ11.04 (s, 1H), 10.28 (s, 1H), 8.06 (s, 1H), 7.62~7.58 (m, 1H), 7.17~7.15 (d, J=8.0 Hz, 1H), 4.89 (s, 1H), 2.73~2.70 (q, J=7.2 Hz, 2H), 2.5~92.51 (m, 1H), 2.3~2.33 (m, 1H), 1.77~1.64 (m, 1H), 0.89~0.74 (m, 6H); Molecular Formula: $C_{14}H_{18}N_6O_3$, Molecular Weight: 318.3, MS (m/z): 319.5.

Example 19

Synthesis of 1-(4-(4-Methyl-6-oxo-1,4,5,6-tetrahydropyridazin-3-yl)-2-nitrophenyl)-3-propylguanidine

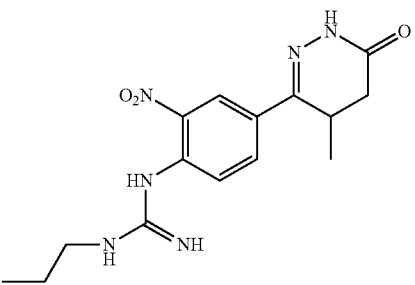 [SMILES: CCCNC(=N)Nc1ccc(C2=NNC(=O)CC2C)cc1[N+](=O)[O-]]

Cyanopropylamine and 6-(4-amino-3-nitrophenyl)-5-methyl 4,5-dihydropyridazine-3(2H)-one were used as raw materials, and the synthesis method was referred to Example 2.

$^1$H NMR (400 MHz, DMSO-d6) δ10.96 (s, 1H), 9.88 (s, 1H), 8.27 (s, 1H), 7.97~7.95 (m, 1H), 7.14~7.12 (d, J=7.6 Hz, 1H), 4.38 (s, 1H), 2.87~2.83 (m, 2H), 2.3~82.29 (m, 2H), 1.75~1.60 (m, 3H), 0.95~0.82 (m, 6H); Molecular Formula: $C_{15}H_{20}N_6O_3$, Molecular Weight: 332.4, MS (m/z): 333.1.

Example 20

Synthesis of 1-isopropyl-3-(4-(4-methyl-6-oxo-1,4,5,6-tetrahydropyridazin-3-yl)-2-nitrophenyl) Guanidine

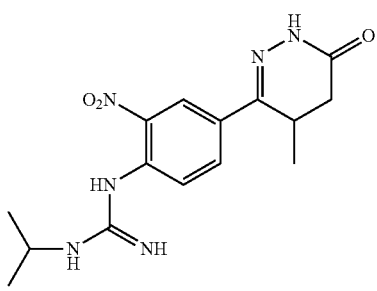 [SMILES: CC(C)NC(=N)Nc1ccc(C2=NNC(=O)CC2C)cc1[N+](=O)[O-]]

N-isopropyl cyanamide and 6-(4-amino-3-nitrophenyl)-5-methyl 4,5-dihydropyridazine-3(2H)-one were used as raw materials, and the synthesis method was referred to Example 2.

$^1$H NMR (400 MHz, DMSO-d6) δ11.05 (s, 1H), 9.82 (s, 1H), 8.05 (s, 1H), 7.91~7.87 (m, 1H), 7.26~7.24 (d, J=8.0 Hz, 1H), 4.92 (s, 1H), 3.25~3.18 (m, 1H), 2.5~72.41 (m, 2H), 1.5~1.48 (m, 1H), 1.19~1.09 (m, 6H), 0.9~0.82 (m, 3H); Molecular Formula: $C_{15}H_{20}N_6O_3$, Molecular Weight: 332.4, MS (m/z): 333.1.

Example 21

Synthesis of 1-Cyclopropyl-3-(4-(4-methyl-6-oxo-1,4,5,6-tetrahydropyridazin-3-yl)-2-nitrophenyl) Guanidine

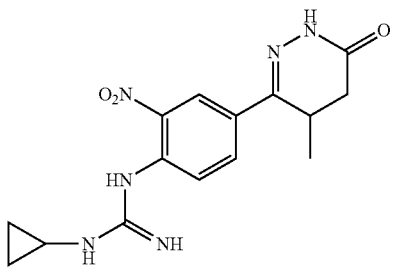 [SMILES: CC1CC(=O)NN=C1c1ccc(NC(=N)NC2CC2)c([N+](=O)[O-])c1]

N-cyclopropylamino cyanide, 6-(4-amino-3-nitrophenyl)-5-methyl 4,5-dihydropyridazine-3(2H)-one were used as raw materials, and the synthesis method was referred to Example 2.

$^1$H NMR (400 MHz, DMSO-d6) δ11.00 (s, 1H), 10.26 (s, 1H), 8.25 (s, 1H), 7.99~7.96 (m, 1H), 7.2~37.18 (m, 1H), 5.08 (s, 1H), 2.51~2.45 (m, 2H), 1.73~1.66 (m, 1H), 1.58~1.42 (m, 1H), 0.9~0.73 (m, 4H); Molecular Formula: $C_{15}H_{18}N_6O_3$, Molecular Weight: 330.3, MS (m/z): 331.2.

Example 22

Synthesis of N—(N-(4-(4-methyl-6-oxo-1,4,5,6-tetrahydropyridazin-3-yl)-2-nitrophenyl)carboxamidino)methanesulfonamide

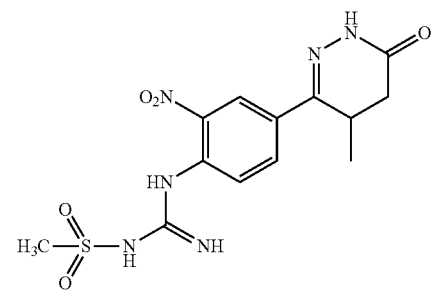 [SMILES: CC1CC(=O)NN=C1c1ccc(NC(=N)NS(C)(=O)=O)c([N+](=O)[O-])c1]

N-cyanomethylsulfonamide and 6-(4-amino-3-nitrophenyl)-5-methyl 4,5-dihydropyridazine-3(2H)-one were used as raw materials, and the synthesis method was referred to Example 2.

$^1$H NMR (400 MHz, DMSO-d6) δ10.88 (s, 1H), 10.02 (s, 1H), 8.07 (s, 1H), 7.82~7.77 (m, 1H), 7.2~17.19 (m, 1H), 4.97 (s, 1H), 3.86 (s, 3H), 2.38~2.24 (m, 1H), 2.17~2.06 (m, 1H), 1.64~1.57 (m, 1H), 0.95 (s, 3H); Molecular Formula: $C_{13}H_{16}N_6O_5S$, Molecular Weight: 368.4, MS (m/z): 369.7.

Example 23 Synthesis of 1-(2-methyl-4-(4-methyl-6-oxo-1,4,5,6-tetrahydropyridazin-3-yl)phenyl)guanidine

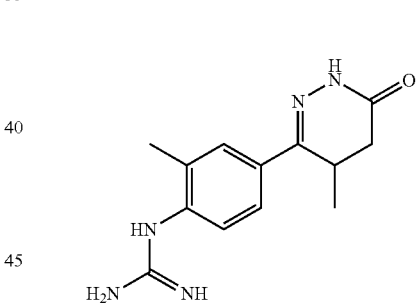

(1) Synthesis of 6-(4-amino-3-methylphenyl)-5-methyl 4,5-dihydropyridazine-3(2H)-one 4-(4-aminophenyl)-3-methyl-4-oxobutanoic acid in Example 1 was replaced by 4-(4-amino-3-methylphenyl)-4-oxobutanoic acid (synthesized by the method of reference INP 2011CH01593), referring to the synthesis method of Example 1.

(2) Synthesis of 1-(2-methyl-4-(4-methyl-6-oxo-1,4,5,6-tetrahydropyridazin-3-yl)phenyl)guanidine Cyanoethylamine and 6-(4-amino-3-methylphenyl)-5-methyl 4,5-dihydropyridazine-3(2H)-one were used as raw materials, referring to the synthesis method of Example 2.

$^1$H NMR (400 MHz, DMSO-d6) δ11.12 (s, 2H), 10.08 (s, 1H), 7.86 (s, 1H), 7.46~7.41 (m, 1H), 6.78~6.76 (d, J=8.0 Hz, 1H), 4.27 (s, 1H), 2.51~2.32 (m, 1H), 2.19~2.07 (m,

1H), 1.7~41.62 (m, 1H), 0.98~0.92 (m, 3H); Molecular Formula: C$_{13}$H$_{17}$N$_5$O, Molecular Weight: 259.3, MS (m/z): 260.2.

Example 24

Synthesis of N—(N-(2-methyl-4-(4-methyl-6-oxo-1,4,5,6-tetrahydropyridazin-3-yl)phenyl)carboxamidino) propionamide

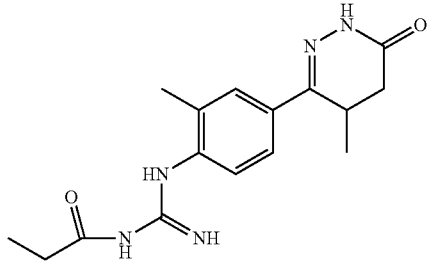 [SMILES: CCC(=O)NC(=N)Nc1ccc(C2=NNC(=O)CC2C)cc1C]

N-cyanopropionamide and 6-(4-amino-3-methylphenyl)-5-methyl 4,5-dihydropyridazine-3(2H)-one were used as raw materials, referring to the synthesis method of Example 2.

$^1$H NMR (400 MHz, DMSO-d6) δ11.08 (s, 2H), 7.77 (s, 1H), 7.52 (s, 1H), 7.41~7.38 (m, 1H), 6.7~16.56 (m, 1H), 4.88 (s, 1H), 2.37~2.32 (m, 3H), 2.14~2.02 (m, 4H), 1.7~91.71 (m, 1H), 0.98~0.92 (m, 6H); Molecular Formula: C$_{16}$H$_{21}$N$_5$O$_2$, Molecular Weight: 315.4, MS (m/z): 316.8.

Example 25

Synthesis of 1-ethyl-3-(2-methyl-4-(4-methyl-6-oxo-1,4,5,6-tetrahydropyridazin-3-yl)phenyl)guanidine

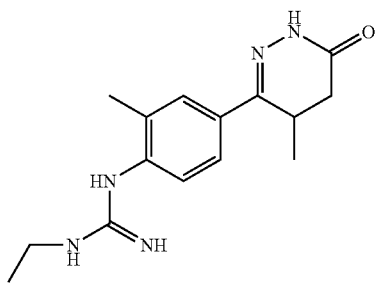 [SMILES: CCNC(=N)Nc1ccc(C2=NNC(=O)CC2C)cc1C]

Cyanoethylamine and 6-(4-amino-3-methylphenyl)-5-methyl 4,5-dihydropyridazine-3(2H)-one were used as raw materials, referring to the synthesis method of Example 2.

$^1$H NMR (400 MHz, DMSO-d6) δ10.87 (s, 1H), 8.37 (s, 1H), 7.48~7.39 (m, 1H), 6.64~6.58 (m, 1H), 4.83 (s, 1H), 2.73~2.71 (q, 2H), 2.33~2.28 (m, 4H), 1.67~1.60 (m, 1H), 0.81~0.72 (m, 6H); Molecular Formula: C$_{15}$H$_{21}$N$_5$O, Molecular Weight: 287.4, MS (m/z): 287.6.

Example 26

Synthesis of 1-(2-methyl-4-(4-methyl-6-oxo-1,4,5,6-tetrahydropyridazin-3-yl)phenyl)-3-propylguanidine

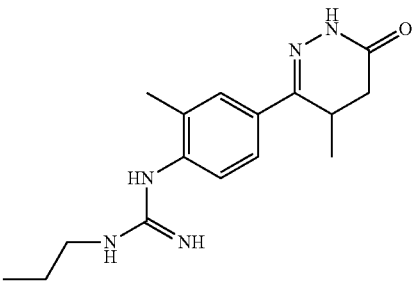 [SMILES: CCCNC(=N)Nc1ccc(C2=NNC(=O)CC2C)cc1C]

Cyanopropylamine and 6-(4-amino-3-methylphenyl)-5-methyl 4,5-dihydropyridazine-3(2H)-one were used as raw materials, referring to the synthesis method of Example 2.

$^1$H NMR (400 MHz, DMSO-d6) δ10.37 (s, 1H), 8.22 (s, 1H), 7.51~7.46 (m, 1H), 6.93~6.88 (m, 1H), 4.38 (s, 1H), 2.93~2.91 (t, 2H), 2.30~2.24 (m, 2H), 2.17 (s, 3H), 1.77~1.60 (m, 3H), 0.8~0.79 (m, 6H); Molecular Formula: C$_{16}$H$_{23}$N$_5$O, Molecular Weight: 301.4, MS (m/z): 302.6.

Example 27

1-isopropyl-3-(2-methyl-4-(4-methyl-6-oxo-1,4,5,6-tetrahydropyridazin-3-yl)phenyl) guanidine

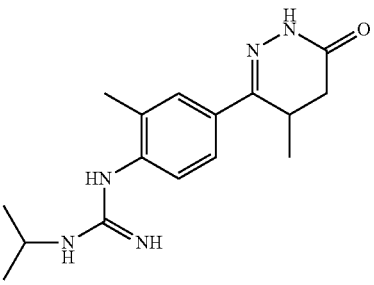 [SMILES: Cc1cc(C2=NNC(=O)CC2C)ccc1NC(=N)NC(C)C]

N-isopropyl cyanamide and 6-(4-amino-3-methylphenyl)-5-methyl 4,5-dihydropyridazine-3(2H)-one were used as raw materials, referring to the synthesis method of Example 2.

$^1$H NMR (400 MHz, DMSO-d6) δ10.57 (s, 1H), 7.51 (s, 1H), 7.37~7.31 (m, 1H), 6.59~6.55 (m, 1H), 5.03 (s, 1H), 3.21~3.14 (m, 1H), 2.38~2.22 (m, 5H), 1.58~1.55 (m, 1H), 1.17~1.15 (s, 6H), 0.9~20.88 (m, 3H); Molecular Formula: C$_{16}$H$_{23}$N$_5$O, Molecular Weight: 301.4, MS (m/z): 302.6.

Example 28

1-cyclopropyl-3-(2-methyl-4-(4-methyl-6-oxo-1,4,5,6-tetrahydropyridazin-3-yl)phenyl) guanidine

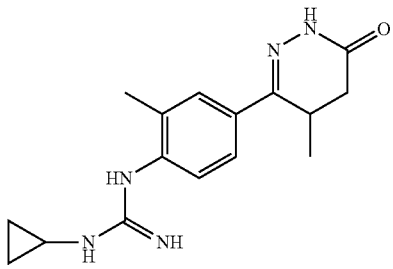 [SMILES: Cc1cc(C2=NNC(=O)CC2C)ccc1NC(=N)NC1CC1]

N-cyclopropyl cyanamide and 6-(4-amino-3-methylphenyl)-5-methyl 4,5-dihydropyridazine-3(2H)-one were used as raw materials, referring to the synthesis method of Example 2.

$^1$H NMR (400 MHz, DMSO-d6) δ10.24 (s, 1H), 7.47 (s, 1H), 7.24~7.19 (m, 1H), 6.61~6.27 (m, 1H), 4.83 (s, 1H), 2.37~2.18 (m, 5H), 1.79~1.70 (m, 2H), 1.06~0.83 (m, 5H), 0.67~0.59 (m, 2H); Molecular Formula: $C_{16}H_{21}N_5O$, Molecular Weight: 299.4, MS (m/z): 300.5.

Example 29

Synthesis of N—(N-(2-methyl-4-(4-methyl-6-oxo-1,4,5,6-tetrahydropyridazin-3-yl)phenyl)carboxamidino)methanesulfonamide

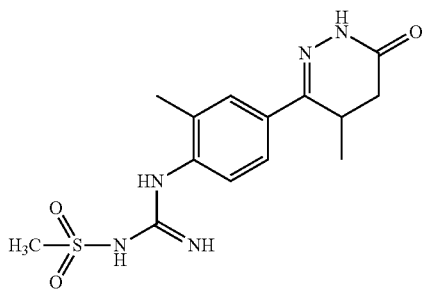 [SMILES: Cc1cc(C2=NNC(=O)CC2C)ccc1NC(=N)NS(C)(=O)=O]

N-cyanomethylsulfonamide and 6-(4-amino-3-methylphenyl)-5-methyl 4,5-dihydropyridazine-3(2H)-one were used as raw materials, referring to the synthesis method of Example 2.

$^1$H NMR (400 MHz, DMSO-d6) δ10.57 (s, 1H), 7.69 (s, 1H), 7.37~7.31 (m, 1H), 6.67~6.62 (m, 1H), 4.55 (s, 1H), 3.04 (s, 3H), 2.35~2.24 (m, 5H), 1.64~1.60 (m, 1H), 1.06~1.01 (m, 3H); Molecular Formula: $C_{14}F_{19}N_5O_3S$, Molecular Weight: 337.4, MS (m/z): 337.6.

The following pharmacological tests are performed on the compounds of this application.

Example 30 Inhibition of Platelet Aggregation In Vitro (Rabbit Blood)

Blood was collected from New Zealand white rabbits (body weight 1-1.5 kg). After the animal was anesthetized with 10% chloral hydrate, the animal was placed supinely on the rabbit board, precordial hair was cut off, and the skin was disinfected with iodine and alcohol. Touch with left hand the 3rd to 4th intercostal space on the left edge of the sternum. Chose the most obvious place for the puncture point. Held the syringe in right hand and insert the needle into the chest cavity. Inserted the needle into the heart and then draw out the blood when feel the heart beating through the needle. Collected the sample in the 3.8 assay system with a total volume of 300 μL, that is, 280 μL of diluted PRP was taken and placed in a turbidimetric tube, and was incubated with 10 μL of drug or solvent control at 37° C. for 5 minutes, and then 10 μL of different inducers such ADP (final concentration 10 μM) were added to determine the maximum platelet aggregation rate within 5 minutes. Repeation was taken at least three times in % sodium citrate (1 volume: 9 volumes of blood).

Platelet-rich plasma (PRP) was obtained by centrifuging blood at 1200 rpm for 10 minutes, and platelet aggregation was measured as described above. The detection of platelet aggregation was carried out by turbidimetric method with Prism LBY-NJ4 platelet aggregation instrument (Beijing Prism Instruments Co., Ltd.). The platelet density in PRP is counted with a hemocytometer and diluted with platelet-poor plasma (PPP). Generally, the platelet density is about 3×108 pieces/mL. Independent experiment. Use the following formula to calculate the inhibitory rate of the drug on platelet aggregation:

Inhibition rate (%)=(aggregation rate control group-aggregation rate administration group)/aggregation rate control group*100

GraphPad Prism software was used to analyze the inhibition rate data obtained at different drug doses, draw a dose-response curve and calculate the half inhibitor amount (IC50) of the drug's inhibitory effect.

The results obtained for each compound were shown in Table 1 below

TABLE 1

| No. | Formula | Inhibition of platelets in vitro (rabbit blood) IC50 (nM) |
|---|---|---|
| 1 | | 197 |
| 2 | | 334 |

TABLE 1-continued

| No. | Formula | Inhibition of platelets in vitro (rabbit blood) IC50 (nM) |
|---|---|---|
| 3 | | 271 |
| 4 | | 248 |
| 5 | | 275 |
| 6 | | 386 |
| 7 | | 595 |
| 8 | | 418 |
| 9 | | 554 |
| 10 | | 615 |
| 11 | | 428 |
| 12 | | 291 |

TABLE 1-continued
| No. | Formula | Inhibition of platelets in vitro (rabbit blood) IC50 (nM) |
|---|---|---|
| 13 | 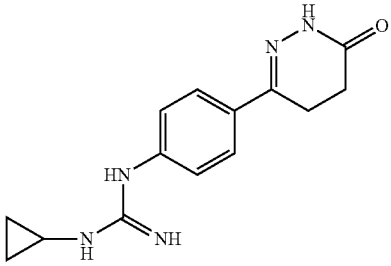 [SMILES: N=C(Nc1ccc(C2=NNC(=O)CC2)cc1)NC1CC1] | 439 |
| 14 | 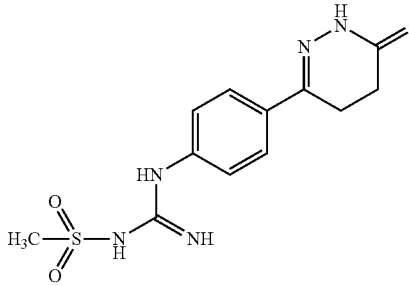 | 557 |
| 15 | 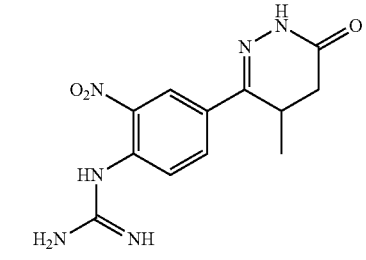 | 712 |
| 16 | 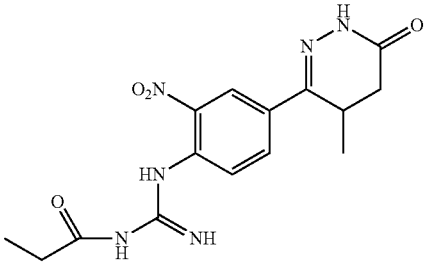 [SMILES: CCC(=O)NC(=N)Nc1ccc(C2=NNC(=O)CC2C)cc1[N+](=O)[O-]] | 648 |
| 17 | 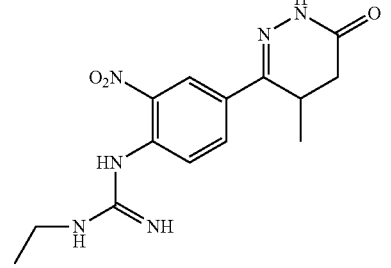 | 653 |
| 18 | 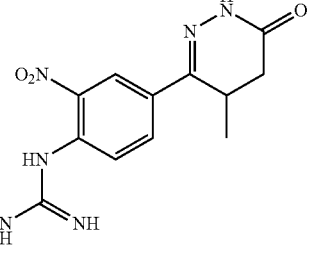 | 612 |
| 19 | 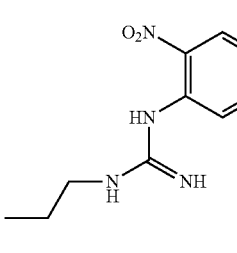 | 573 |
| 20 | 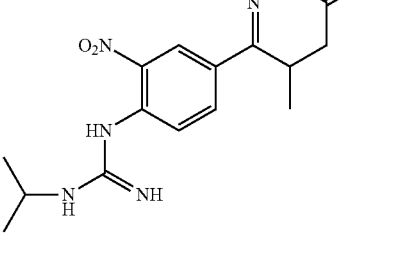 | 664 |
| 21 | 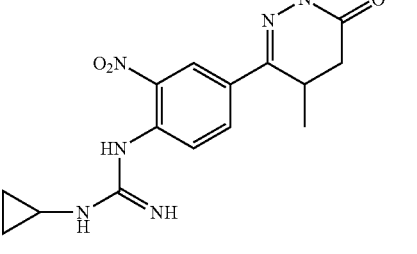 | 484 |
| 22 | 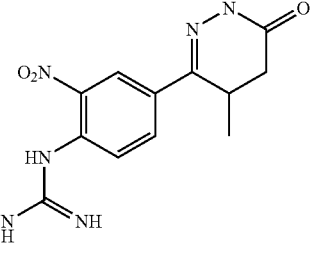 | 351 |

TABLE 1-continued

| No. | Formula | Inhibition of platelets in vitro (rabbit blood) IC50 (nM) |
|---|---|---|
| 23 | (structure) | 387 |
| 24 | (structure) | 458 |
| 25 | (structure) | 442 |
| 26 | (structure) | 405 |
| 27 | (structure) | 291 |
| 28 | (structure) | 354 |

Example 31

The inhibitory effect of compound No. 1 (the compound numbers are listed in Table 1 above) on ADP-induced aggregation of human platelets.

Volunteers' whole blood was drawn from venous blood with 1:6 dextro-citrate ACD (85 mmol/L sodium citrate, 71.38 mmol/L citrate, 27.78 mmol/L glucose) for anticoagulation, and centrifuged at 300 g at room temperature for 10 minutes, platelet rich plasma (PRP) was separated.

The turbidimetric platelet aggregation test was performed on the Chrono-Log Company's dual-channel optical platelet aggregation instrument. The speed of the icon recorder was set to 1 cm/min, and the aggregation curve was recorded. First, the platelet aggregator was preheated to 37° C., 400 μL platelet suspension and stir bar were added to the turbidity tube, use PPP as a reference, and traced the baseline under constant magnetic stirring at 37° C. After the baseline was stable, with experiment plan, different concentrations of antagonists or other reagents were added to treat platelets for 2 minutes, and then the inducer ADP was added to observe and record changes in the aggregation curve.

TABLE 2

Effects of different concentrations of compounds on the rate of platelet aggregation induced by 10 μM ADP

| Drug name | Concentration (μM) | Aggregation inhibition rate % |
|---|---|---|
| Ticagrelor (μM) | 0.03 | 49.15 |
| | 0.1 | 41.17 |
| | 0.3 | 82.35 |
| | 1 | 100 |
| | 3 | 100 |
| | 5 | 100 |
| | 10 | 100 |
| No.1 Compound (μM) | 0.03 | 49.01 |
| | 0.1 | 43.13 |
| | 0.3 | 62.74 |
| | 1 | 66.67 |
| | 3 | 71.56 |
| | 5 | 81.37 |
| | 10 | 95.09 |

TABLE 2-continued

Effects of different concentrations of compounds on the rate of platelet aggregation induced by 10 μM ADP

| Drug name | Concentration (μM) | Aggregation inhibition rate % |
|---|---|---|
| Ticagrelor (μM) | 0.005 | 0 |
| | 0.01 | 4.11 |
| | 0.03 | 13.69 |
| | 0.1 | 15.06 |
| | 0.3 | 20.54 |
| | 1 | 57.53 |
| | 3 | 86.30 |
| Compound No.1 (μM) | 0.005 | 2.99 |
| | 0.01 | 8.69 |
| | 0.03 | 17.39 |
| | 0.1 | 37.68 |
| | 0.3 | 39.13 |
| | 1 | 42.02 |
| | 3 | 51.88 |
| Ticagrelor (μM) | 0.005 | 0 |
| | 0.01 | 4.11 |
| | 0.03 | 13.69 |
| | 0.1 | 15.06 |
| | 0.3 | 20.54 |
| | 1 | 57.53 |
| | 3 | 86.30 |
| Compound No.1 (μM) | 0.005 | 2.99 |
| | 0.01 | 8.69 |
| | 0.03 | 17.39 |
| | 0.1 | 37.68 |
| | 0.3 | 39.13 |
| | 1 | 42.02 |
| | 3 | 51.88 |

TABLE 3

$IC_{50}$ of compound on ADP-induced platelet aggregation rate

| IC50(μM) | 1 | 2 | 3 |
|---|---|---|---|
| Ticagrelor | 0.072 | 0.963 | 0.261 |
| Compound No.1 | 0.097 | 1.075 | 0.154 |

Example 32

The inhibitory effect of compound No. 1 on thrombin-induced human platelet aggregation.

Volunteers' whole blood was drawn from venous blood with 1:6 D-citrate ACD (85 mmol/L sodium citrate, 71.38 mmol/L citrate, 27.78 mmol/L glucose) for anticoagulation, and centrifuged at 300 g at room temperature for 10 minutes, platelet rich plasma (PRP) was separated.

The turbidimetric platelet aggregation test was performed on the Chrono-Log Company's dual-channel optical platelet aggregation instrument. The speed of the icon recorder was set to 1 cm/min, and the aggregation curve was recorded. First, the platelet aggregator was preheated to 37° C., and 400 μL platelet suspension and stir bar were added to the turbidity tube, PPP was used as a reference, and traced the baseline under constant magnetic stirring at 37° C. After the baseline is stable, with the experiment plan, different concentrations of antagonists or other reagents were added to treat platelets for 2 minutes, and then the inducer ADP was added to observe and record changes in the aggregation curve.

TABLE 4

Effect of Compound No. 1 in Different Concentrations on Platelet Aggregation Induced by 0.5 U/ml Thrombin

| Drug Name | Concentration (μM) | Aggregation inhibition rate % |
|---|---|---|
| Ticagrelor (μM) | 0.03 | 6.35 |
| | 0.1 | 20.63 |
| | 0.3 | 39.68 |
| | 1 | 47.62 |
| | 3 | 69.84 |
| | 10 | 80.95 |
| | 20 | 95.23 |
| Compound No.1 (μM) | 0.03 | 7.14 |
| | 0.1 | 46.03 |
| | 0.3 | 71.42 |
| | 1 | 85.71 |
| | 3 | 100 |
| | 10 | 100 |
| | 20 | 100 |
| Ticagrelor (μM) | 0.003 | 0 |
| | 0.01 | 0 |
| | 0.03 | 2.67 |
| | 0.1 | 4.02 |
| | 0.3 | 6.76 |
| | 1 | 39.18 |
| | 3 | 49.33 |
| | 10 | 55.41 |
| | 20 | 81.33 |
| Compound No.1 (μM) | 0.003 | 0 |
| | 0.01 | 3.08 |
| | 0.03 | 6.15 |
| | 0.1 | 40.98 |
| | 0.3 | 80.95 |
| | 1 | 95.83 |
| | 3 | 100 |
| Ticagrelor (μM) | 0.01 | 0 |
| | 0.03 | 19.71 |
| | 0.1 | 46.47 |
| | 0.3 | 63.38 |
| | 1 | 84.50 |
| | 3 | 92.53 |
| | 10 | 100 |
| Compound No.1 (μM) | 0.01 | 2.81 |
| | 0.03 | 36.62 |
| | 0.1 | 65.21 |
| | 0.3 | 89.85 |
| | 1 | 97.33 |
| | 3 | 100 |
| | 10 | 100 |

TABLE 5

IC50 of compound No. 1 on thrombin-induced platelet aggregation rate

| $IC_{50}$ (μM) | 1 | 2 | 3 |
|---|---|---|---|
| Ticagrelor | 0.851 | 4.016 | 0.161 |
| Compound No.1 | 0.194 | 0.140 | 0.078 |

Example 33

The inhibitory effect of compound No. 1 on collagen-induced aggregation of human platelets.

Volunteers' whole blood was drawn from venous blood with 1:6 dextro-citrate ACD (85 mmol/L sodium citrate, 71.38 mmol/L citrate, 27.78 mmol/L glucose) for anticoagulation, and centrifuged at 300 g at room temperature for 10 Minutes, separate platelet rich plasma (PRP).

The turbidimetric platelet aggregation test was performed on the Chrono-Log Company's dual-channel optical platelet aggregation instrument. The speed of the icon recorder was set to 1 cm/min, and the aggregation curve was recorded. First, the platelet aggregator was preheated to 37° C., and 400 μL platelet suspension and stir bar were added to the turbidity tube, PPP was used as a reference, and traced the baseline under constant magnetic stirring at 37° C. After the baseline was stable, with the experiment plan, different concentrations of antagonist or other reagents were added to treat platelets for 2 minutes, and then inducer collagen was added to observe and record changes in the aggregation curve.

The platelet aggregation rate of the solvent control group was set to be 100%. The inhibitory effects of the compounds on normal human platelet aggregation induced by collagen at different concentrations were as follows:

TABLE 6

Effects of different concentrations of compounds on the rate of platelet aggregation induced by 1 μg/ml collagen

| Drug Name | Concentration (μM) | Aggregation inhibition rate % |
|---|---|---|
| Ticagrelor (μM) | 0.003 | 1.45 |
|  | 0.01 | 8.69 |
|  | 0.03 | 13.04 |
|  | 0.1 | 14.49 |
|  | 0.3 | 15.94 |
|  | 1 | 20.28 |
|  | 3 | 75.36 |
|  | 10 | 82.60 |
| Compound No.1 (μM) | 0.003 | 5.97 |
|  | 0.01 | 10.45 |
|  | 0.03 | 14.93 |
|  | 0.1 | 30.43 |
|  | 0.3 | 79.10 |
|  | 1 | 95.89 |
|  | 3 | 100 |
| Ticagrelor (μM) | 0.003 | 0 |
|  | 0.01 | 2.98 |
|  | 0.03 | 8.95 |
|  | 0.1 | 29.85 |
|  | 0.3 | 53.73 |
|  | 1 | 55.88 |
|  | 3 | 66.17 |
|  | 10 | 75 |
|  | 20 | 100 |
| Compound No.1 (μM) | 0.03 | 7.46 |
|  | 0.01 | 8.96 |
|  | 0.03 | 13.43 |
|  | 0.1 | 16.42 |
|  | 0.3 | 44.78 |
|  | 1 | 80.59 |
|  | 3 | 100 |
| Ticagrelor (μM) | 0.003 | 4.23 |
|  | 0.01 | 9.86 |
|  | 0.03 | 15.49 |
|  | 0.1 | 17.91 |
|  | 0.3 | 28.16 |
|  | 1 | 35.21 |
|  | 3 | 64.78 |
|  | 10 | 92.95 |
| Compound No.1 (μM) | 0.03 | 6.25 |
|  | 0.01 | 10.94 |
|  | 0.03 | 18.75 |
|  | 0.1 | 40.62 |
|  | 0.3 | 54.69 |
|  | 1 | 95.31 |
|  | 3 | 100 |

TABLE 7

IC50 of compound on collagen-induced platelet aggregation rate

| $IC_{50}$ (μM) | 1 | 2 | 3 |
|---|---|---|---|
| Ticagrelor | 0.888 | 0.532 | 0.908 |
| Compound No.1 | 0.095 | 0.233 | 0.143 |

The results showed that the compound No. 1 has a significant inhibitory effect on platelet aggregation induced by 1 μg/ml collagen ($IC_{50}$: 0.157 μM).

Example 34

Inhibitory effect of compound number 1 given by gavage on platelet aggregation in male SD rats.

The blood was taken from the abdominal aorta of male SD rats by intragastric administration for 4 hours and centrifuged at 300 g for 10 min to prepare PRP.

The turbidimetric platelet aggregation test was performed on the Chrono-Log Company's dual-channel optical platelet aggregation instrument. The speed of the icon recorder was set to 1 cm/min, and the aggregation curve was recorded. First, the platelet aggregator was preheated to 37° C., and 400 μL of platelet suspension and stir bar were added to the turbidimetric tube, PPP was used as a reference, and traced the baseline under constant magnetic stirring at 37° C. After the baseline is stable, induction was added to observe and record changes in the aggregation curve.

Example 35

Effect of compound No. 1 administered intragastrically on arterial thrombosis in male SD rats.

Cut the surgical wire with a length of 6 cm, weigh and recorded it on an analytical balance (about 2 mg dry weight), and placed it in a thick polyethylene tube with a length of 6 cm. Inserted a thin tube at each end of the thick tube spare. Male SD rats were intragastrically administered for 4 hours, anesthetized with pentobarbital 60 mg/kg, separated the common carotid artery and common jugular vein, connected the arteries and veins with the above polyethylene tube, opened the blood flow for 15 minutes, removed the surgical line and weighed ($W_W$).

TABLE 8

SD male rat arteriovenous short circuit thrombosis model (A-V shunt)

| Drug Name | Dose (mg/kg) | Thrombus wet weight (mg) |
|---|---|---|
| Vehicle | / | 20.9 |
|  |  | 18.7 |
|  |  | 19.6 |
| Compound No.1 | 10 | 11.7 |
|  |  | 11.5 |
|  |  | 12.1 |

By intragastric administration of compound No. 1, the weight of arterial thrombus in rats was significantly reduced.

The compounds of the application are ingredients with significant activity, which are compatible with their use as medicines and/or pharmaceutical compositions.

What is claimed is:

1. A compound of Formula (I):

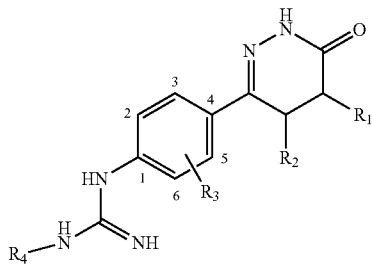

wherein
positions on a benzene ring are numbered 1-6 respectively, R1 is selected from: hydrogen, halogen, nitro, cyano; C1-C6 alkyl optionally substituted by halogen, nitro, cyano; C1-C6 oxygen-containing alkyl; C3-C7 cycloalkyl optionally substituted by halogen, nitro, cyano; —O—C1-C6 alkyl optionally substituted by halogen, nitro, amino, cyano;

—O—C3-C7 cycloalkyl optionally substituted by halogen, nitro, amino, cyano; C6-C10 aryl optionally substituted by halogen, nitro, amino, cyano; —O—C6-C10 aryl optionally substituted by halogen, nitro, amino, cyano; C2-C6 alkenyl;

R2 is selected from: hydrogen, halogen, nitro, cyano; C1-C6 alkyl optionally substituted by halogen, nitro, cyano; C1-C6 alkoxyl; C3-C7 cycloalkyl optionally substituted by halogen, nitro, cyano; —O—C1-C6 alkyl optionally substituted by halogen, nitro, amino, cyano; —O—C3-C7 cycloalkyl optionally substituted by halogen, nitro, amino, cyano; C6-C10 aryl optionally substituted by halogen, nitro, amino, cyano; —O—C6-C10 aryl optionally substituted by halogen, nitro, amino, cyano; C2-C6 alkenyl;

R3 is selected from: hydrogen, halogen, nitro, cyano, amino, hydroxyl; substituted or unsubstituted C1-C6 alkyl, substituted or unsubstituted C3-C7 cycloalkyl, C3-C7 cycloalkyl, C1-C6 Alkyl, heterocyclicC1-C6 alkyl, substituted or unsubstituted C6-C10 aryl, C9-C12 bicyclic aryl, heteroC6-C12 bicyclic aryl, heteroC6-C12 bicyclic arylC1-C3 alkyl, C6-C10 aryl C1-C3 alkyl, substituted or unsubstituted C6-C10 aryl C1-C6 alkyl, substituted or unsubstituted heteroaryl, substituted or unsubstituted heteroaryl C1-C6 alkyl, carbonylC1-C6 alkyl, thiocarbonylC 1-C 6 alkyl, sulfonylC 1-C3 alkyl, sulfinylC 1-C 6 alkyl, iminoC 1-C 6 alkyl, —O—C 1-C6 alkyl;

R4 is selected from: hydrogen; C1-C6 alkyl optionally substituted by halogen, nitro, cyano; C1-C6 oxygen-containing alkyl; C3-C7 cycloalkyl optionally substituted by halogen, nitro, cyano; —O—C1-C6 alkyl optionally substituted by halogen, nitro, amino, cyano; —O—C3-C7 cycloalkyl optionally substituted by halogen, nitro, amino, cyano; C6-C10 aryl optionally substituted by halogen, nitro, amino, cyano; —O—C6-C10 aryl optionally substituted by halogen, nitro, amino, cyano; C2-C6 alkenyl; C3-C6 acyl; C1-C6 alkylsulfonyl.

2. The compound of claim 1 is selected from following compounds, wherein the compounds are selected from following:

| No. | Name | Formula |
|---|---|---|
| 1 | 1-(4-(4-methyl-6-oxo-1,4,5,6-tetrahydropyridazine-3-yl)phenyl)guanidine | 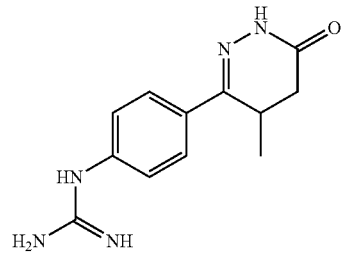 [SMILES: CC1CC(=O)NN=C1c1ccc(NC(=N)N)cc1] |
| 2 | N-(N-(4-(4-methyl-6-oxo-1,4,5,6-tetrahydropyridazine-3-yl)phenyl)carboxamidino)propionamide | 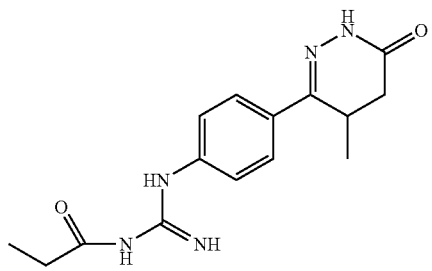 [SMILES: CCC(=O)NC(=N)Nc1ccc(C2=NNC(=O)CC2C)cc1] |

-continued

| No. | Name | Formula |
|---|---|---|
| 3 | 1-ethyl-3-(4-(4-methyl-6-oxo-1,4,5,6-tetrahydropyridazine-3-yl)phenyl)guanidine | 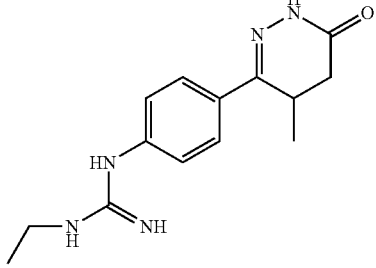 |
| 4 | 1-(4-(4-methyl-6-oxo-1,4,5,6-tetrahydropyridazine-3-yl)phenyl)-3-propylguanidine | 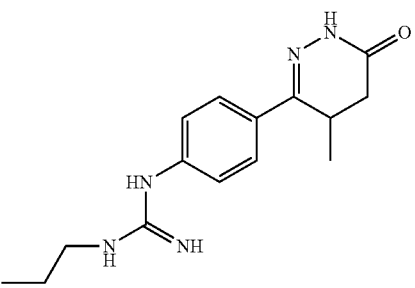 [SMILES: CCCNC(=N)Nc1ccc(C2=NNC(=O)CC2C)cc1] |
| 5 | 1-isopropyl-3-(4-(4-methyl-6-oxo-1,4,5,6-tetrahydropyridazine-3-yl)phenyl)guanidine | 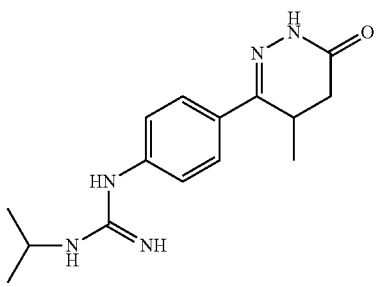 [SMILES: CC(C)NC(=N)Nc1ccc(C2=NNC(=O)CC2C)cc1] |
| 6 | 1-cyclopropyl-3-(4-(4-methyl-6-oxo-1,4,5,6-tetrahydropyridazine-3-yl)phenyl)guanidine | 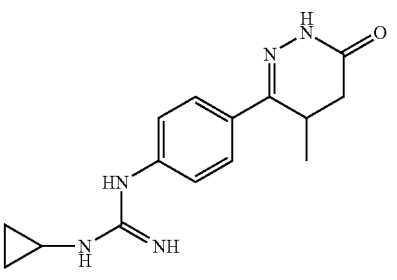 [SMILES: CC1CC(=O)NN=C1c1ccc(NC(=N)NC2CC2)cc1] |
| 7 | N-(N-(4-(4-methyl-6-oxo-1,4,5,6-tetrahydropyridazine-3-yl)phenyl)amidino)methanesulfonamide | 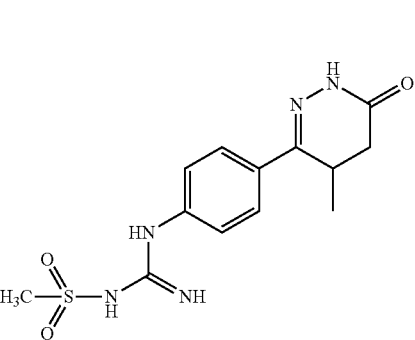 [SMILES: CC1CC(=O)NN=C1c1ccc(NC(=N)NS(C)(=O)=O)cc1] |

-continued

| No. | Name | Formula |
|---|---|---|
| 8 | 1-(4-(6-oxo-1,4,5,6-tetrahydropyridazine-3-yl)phenyl)guanidine | |
| 9 | N-(N-(4-(6-oxo-1,4,5,6-tetrahydropyridazin-3-yl)phenyl)amidino)propionamide | |
| 10 | 1-ethyl-3-(4-(6-oxo-1,4,5,6-tetrahydropyridazine-3-yl)phenyl)guanidine | |
| 11 | 1-(4-(6-oxo-1,4,5,6-tetrahydropyridazine-3-yl)phenyl)-3-propylguanidine | |
| 12 | 1-isopropyl-3-(4-(6-oxo-1,4,5,6-tetrahydropyridazine-3-yl)phenyl)guanidine | |

| No. | Name | Formula |
|---|---|---|
| 13 | 1-cyclopropyl-3-(4-(6-oxo-1,4,5,6-tetrahydropyridazine-3-yl)phenyl)guanidine | 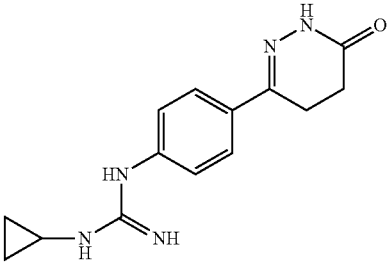 [SMILES: N=C(Nc1ccc(C2=NNC(=O)CC2)cc1)NC1CC1] |
| 14 | N-(N-(4-(6-oxo-1,4,5,6-tetrahydropyridazine-3-yl)phenyl)amidino)methanesulfonamide | 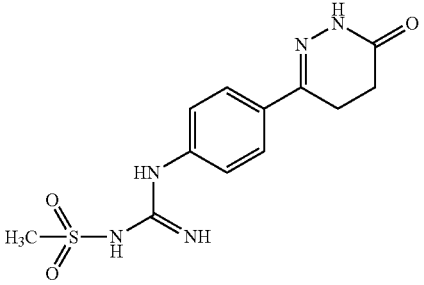 |
| 15 | 1-(4-(4-methyl-6-oxo-1,4,5,6-tetrahydropyridazine-3-yl)-2-nitrophenyl)guanidine | 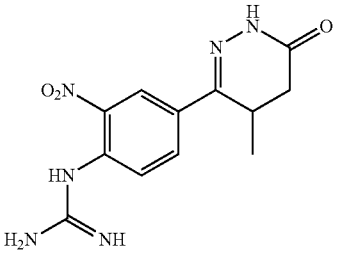 [SMILES: CC1CC(=O)NN=C1c1ccc(NC(=N)N)c([N+](=O)[O-])c1] |
| 16 | N-(N-(4-(4-methyl-6-oxo-1,4,5,6-tetrahydropyridazine-3-yl)-2-nitrophenyl)amidino)propionamide | 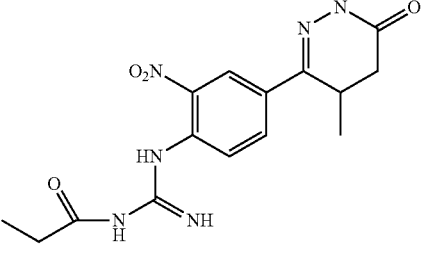 |
| 17 | 1-ethyl-3-(4-(4-methyl-6-oxo-1,4,5,6-tetrahydropyridazine-3-yl)-2-nitrophenyl)guanidine | 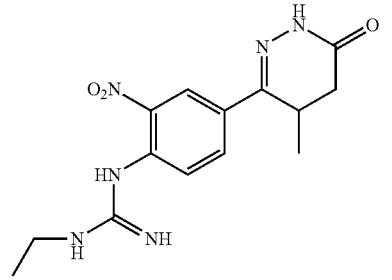 [SMILES: CCNC(=N)Nc1ccc(C2=NNC(=O)CC2C)cc1[N+](=O)[O-]] |

| No. | Name | Formula |
|---|---|---|
| 18 | 1-(4-(4-methyl-6-oxo-1,4,5,6-tetrahydropyridazine-3-yl)-2-nitrophenyl)-3-propylguanidine | 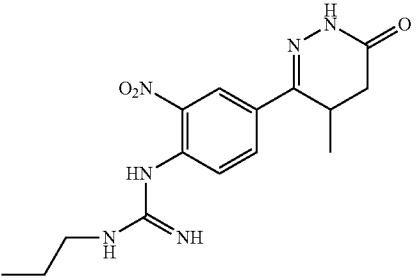 |
| 19 | 1-isopropyl-3-(4-(4-methyl-6-oxo-1,4,5,6-tetrahydropyridazine-3-yl)-2-nitrophenyl)guanidine | 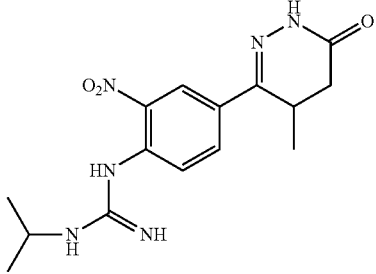 [SMILES: CC(C)NC(=N)Nc1ccc(C2=NNC(=O)CC2C)cc1[N+](=O)[O-]] |
| 20 | 1-cyclopropyl-3-(4-(4-methyl-6-oxo-1,4,5,6-tetrahydropyridazine-3-yl)-2-nitrophenyl)guanidine | 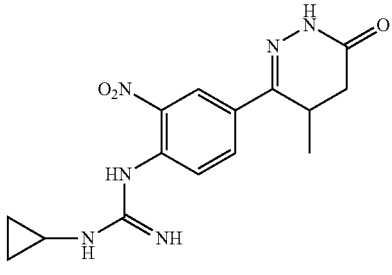 [SMILES: CC1CC(=O)NN=C1c1ccc(NC(=N)NC2CC2)c([N+](=O)[O-])c1] |
| 21 | N-(N-(4-(4-Methyl-6-oxo-1,4,5,6-tetrahydropyridazine-3-yl)-2-nitrophenyl)amidino)methanesulfonamide | 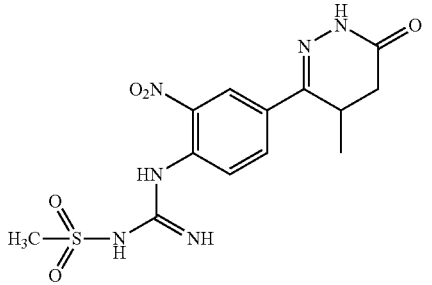 [SMILES: CC1CC(=O)NN=C1c1ccc(NC(=N)NS(C)(=O)=O)c([N+](=O)[O-])c1] |
| 22 | 1-(2-methyl-4-(4-methyl-6-oxo-1,4,5,6-tetrahydropyridazine-3-yl)phenyl)guanidine | 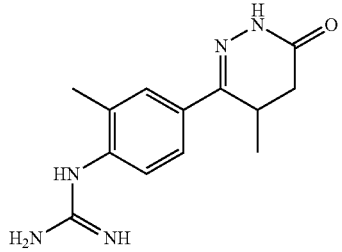 [SMILES: Cc1cc(C2=NNC(=O)CC2C)ccc1NC(=N)N] |

-continued

| No. | Name | Formula |
|---|---|---|
| 23 | N-(N-(2-methyl-4-(4-methyl-6-oxo-1,4,5,6-tetrahydropyridazine-3-yl)phenyl)amidino)propionamide | 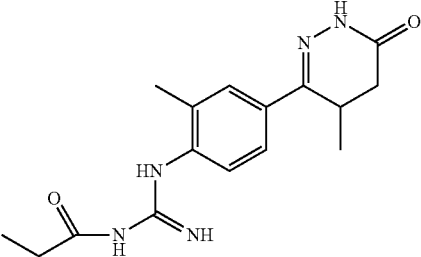 [SMILES: CCC(=O)NC(=N)Nc1ccc(C2=NNC(=O)CC2C)cc1C] |
| 24 | 1-ethyl-3-(2-methyl-4-(4-methyl-6-oxo-1,4,5,6-tetrahydropyridazine-3-yl)phenyl)guanidine | 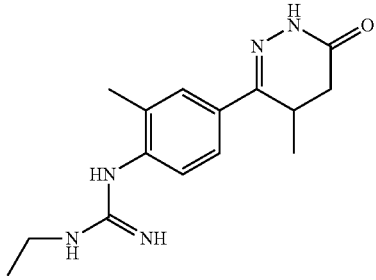 [SMILES: CCNC(=N)Nc1ccc(C2=NNC(=O)CC2C)cc1C] |
| 25 | 1-(2-methyl-4-(4-methyl-6-oxo-1,4,5,6-tetrahydropyridazine-3-yl)phenyl)-3-propylguanidine | 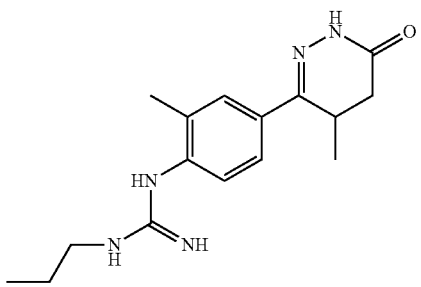 [SMILES: CCCNC(=N)Nc1ccc(C2=NNC(=O)CC2C)cc1C] |
| 26 | 1-isopropyl-3-(2-methyl-4-(4-methyl-6-oxo-1,4,5,6-tetrahydropyridazine-3-yl)phenyl)guanidine | 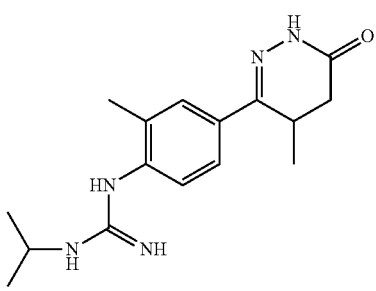 [SMILES: Cc1cc(C2=NNC(=O)CC2C)ccc1NC(=N)NC(C)C] |
| 27 | 1-cyclopropyl-3-(2-methyl-4-(4-methyl-6-oxo-1,4,5,6-tetrahydropyridazine-3-yl)phenyl)guanidine | 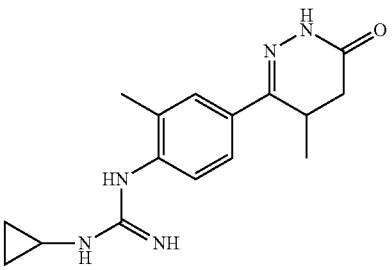 [SMILES: Cc1cc(C2=NNC(=O)CC2C)ccc1NC(=N)NC1CC1] |

-continued

| No. | Name | Formula |
|---|---|---|
| 28 | N-(N-(2-methyl-4-(4-methyl-6-oxo-1,4,5,6-tetrahydropyridazine-3-yl)phenyl)amidino)methanesulfonamide | |

* * * * *